US007211600B2

(12) United States Patent
Lipson et al.

(10) Patent No.: US 7,211,600 B2
(45) Date of Patent: May 1, 2007

(54) METHODS OF MODULATING C-KIT TYROSINE PROTEIN KINASE FUNCTION WITH INDOLINONE COMPOUNDS

(75) Inventors: Ken Lipson, San Mateo, CA (US); Gerald McMahon, Kenwood, CA (US)

(73) Assignee: Sugen Inc., South San Francisco, CA (US)

( * ) Notice: Subject to any disclaimer, the term of this patent is extended or adjusted under 35 U.S.C. 154(b) by 0 days.

(21) Appl. No.: 11/205,474

(22) Filed: Aug. 16, 2005

(65) Prior Publication Data
US 2005/0288353 A1 Dec. 29, 2005

Related U.S. Application Data

(63) Continuation of application No. 10/600,868, filed on Jun. 23, 2003, now abandoned, which is a continuation of application No. 09/741,842, filed on Dec. 22, 2000, now abandoned.

(60) Provisional application No. 60/171,963, filed on Dec. 22, 1999.

(51) Int. Cl.
*A01N 43/38* (2006.01)
(52) U.S. Cl. .................. 514/418; 514/312; 514/414; 514/404; 514/469
(58) Field of Classification Search .................. None
See application file for complete search history.

(56) References Cited

U.S. PATENT DOCUMENTS

| 4,376,110 | A | 3/1983 | David et al. |
| 4,966,849 | A | 10/1990 | Vallee et al. |
| 5,217,999 | A | 6/1993 | Levitzki et al. |
| 5,330,992 | A | 7/1994 | Eissenstat et al. |
| 5,792,783 | A | 8/1998 | Tang et al. |
| 5,883,116 | A | 3/1999 | Tang et al. |
| 5,905,149 | A | 5/1999 | Battistini et al. |
| 6,339,100 | B1 | 1/2002 | Longley |
| 6,395,734 | B1 | 5/2002 | Tang et al. |
| 6,514,981 | B1 | 2/2003 | Tang et al. |
| 6,689,806 | B1* | 2/2004 | Tang et al. .................. 514/418 |
| 6,878,733 | B1 | 4/2005 | Shenoy et al. |

FOREIGN PATENT DOCUMENTS

| WO | WO 91/15495 | 10/1991 |
| WO | WO 92/20642 | 11/1992 |
| WO | WO 92/21660 | 12/1992 |
| WO | WO 94/03427 | 2/1994 |
| WO | WO 94/10202 | 5/1994 |
| WO | WO 94/14808 | 7/1994 |
| WO | WO 96/22976 | 8/1996 |
| WO | WO 98/07695 | 2/1998 |
| WO | WO 99/06468 | 2/1999 |
| WO | WO 99/10325 | 3/1999 |
| WO | WO 99/61422 | 12/1999 |

OTHER PUBLICATIONS

Akbasak, A., "Oncogenes: Cause Or Consequence In The Development Of Glial Tumors," *Journal of the Neurological Sciences*, 1992, 119-133, vol. 111.
Andoh, A., "Rapid Intestinal Ischaemia-Reperfusion Injury Is Suppressed In Genetically Mast Cell-Deficient Ws/Ws Rats," *Clinical Experimental Immunology*, 1999, 90-93, vol. 116.
Beck, D., "Expression Of Stem Cell Factor And Its Receptor By Human Neuroblastoma Cells And Tumors," *Blood*, 1995, 3132-3138, vol. 86, No. 8.
Bedi, A., "BCR-ABL-Mediated Inhibition Of Apoptosis With Delay Of G2/M Transition After DNA Damage: A Mechanism Of Resistance To Multiple Anticancer Agents," *Blood*, 1995, 1148-1158, vol. 86, No. 3.
Bellone, G., "Growth Stimulation Of Colorectal Carcinoma Cells Via The c-Kit Receptor Is Inhibited By TGF-β1," *Journal of Cellular Physiology*, 1997, 1-11, vol. 172.
Berdel, W., "Recombinant Human Stem Cell Factor Stimulates Growth Of A Human Glioblastoma Cell Line Expressing c-Kit Protooncogene," *Cancer Research*, 1992, 3498-3502, vol. 52.
Blume-Jensen, P., "Kit/Stem Cell Factor Receptor-Induced Activation Of Phosphatidylinositol 3'-Kinase is Essential for Male Fertility," *Nature Genetics*, 2000, 157-162, vol. 24.
Bokemeyer, C., "Expression Of Stem-Cell Factor And Its Receptor c-Kit Protein In Normal Testicular Tissue And Malignant Germ-Cell Tumours," *Journal of Cancer Research and Clinical Oncology*, 1996, 301-306, vol. 122.
Broudy, V., "Stem Cell Factor and Hematopoiesis," *Blood*, 1997, 1345-1364, vol. 90, No. 4.
Carpino, N., "p62$^{dok}$: A Constitutively Tyrosine-Phosphorylated, GAP-Associated Protein In Chronic Myelogenous Leukemia Progenitor Cells," *Cell*, 1997, 197-204, vol. 88.
Castells, M., "The Presence Of Membrane-Bound Stem Cell Factor On Highly Immagture Nonmetachromatic Mast Cells In The Peripheral Blood Of A Patient With Aggressive Systemic Mastocytosis," *Journal of Allergy and Clinical Immunology*, 1996, 831-840, vol. 98, No. 4.
Chao, M., "Growth Factor Signaling: Where Is The Specificity?" *Cell*, 1992, 995-997, vol. 68.
Cohen, P., "Expression Of Stem Cell Factor And c-Kit In Human Neuroblastoma," *Blood*, 1994, 3465-3472, vol. 84, No. 10.
Columbo, M., "The Human Recombinant c-Kit Receptor Ligand, rhSCF, Induces Mediator Release From Human Cutaneous Mast Cells And Enhances IgE-Dependent Mediator Release From Both Skin Mast Cells And Peripheral Blood Basophils," *The Journal of Immunology*, 1992, 599-608, vol. 149, No. 2.
Costa, J., "The Cells Of The Allergic Response," *JAMA*, 1997, 1815-1822, vol. 278, No. 22.
Dastych, J., "Stem Cell Factor Induces Mast Cell Adhesion To Fibronectin," Journal of Immunology, 1994, 213-219, vol. 152.

(Continued)

*Primary Examiner*—Ardin H. Marschel
*Assistant Examiner*—Shirley V. Gembeh
(74) *Attorney, Agent, or Firm*—Bryan C. Zielinski; Vincent P. Liptak

(57) ABSTRACT

The present invention concerns compounds and their use to inhibit the activity of a receptor tyrosine kinase. The invention is preferably used to treat cell proliferative disorders such as cancers characterized by over-activity or inappropriate activity c-kit kinase.

4 Claims, 2 Drawing Sheets

OTHER PUBLICATIONS

Dickson, R., "Tyrosine Kinase Receptor—Nuclear Protooncogene Interactions In Breast Cancer," *Genes, Oncogenes, and Hormones: Advances In Cellular And Molecular Biology of Breast Cancer*, 1991, 249-273, Kluwer Academic Publishers, Boston.

Driancourt, M., "Roles Of Kit and Kit Ligand In Ovarian Function," *Reviews of Reproduction*, 2000, 143-152, vol. 5.

Dyson, N., "The Human Papilloma Virus—16 E7 Oncoprotein Is Able To Bind To The Retinoblastoma Gene Product," *Science*, 1989, 934-937, vol. 243.

Escribano, L., "Expression of the C-Kit (CD117) Molecule In Normal And Malignant Hematopoiesis," *Leukemia and Lymphoma*, 1998, 459-466, vol. 30.

Feng, H., "Decreased Expression Of The C-Kit Receptor Is Associated With Increased Apoptosis In Subfertile Human Testes," *Fertility and Sterility*, 1999, 85-89, vol. 71, No. 1.

Finotto, S., "Glucocorticoids Decrease Tissue Mast Cell Number By Reducing The Production Of the C-Kit Ligand, Stem cell Factor, By Resident Cells," *The Journal of Clinical Investigation*, 1997, 1721-1728, vol. 99, No. 7.

Furitsu, T., "Identification Of Mutations In The Code Sequence Of The Prot-Oncogene C-Kit in A Human Mast Cell Leukemia Cell Line Causing Ligand-Independent Activiation of C-Kit Product," *Journal of Clinical Investigation*, 1993, 1736-1744, vol. 92.

Furuta, G., "Stem Cell Factor Influences Mast Cell Mediator Release In Response To Eosinophil-Derived Granule Major Basic Protein," *Blood*, 1998, 1055-1061, vol. 92, No. 3.

Gaca, M., "Human And Rat Hepatic Stellate Cells Produce Stem Cell Factor: A Possible Mechanism For Mast Cell Recruitment In Liver Fibrosis," *Journal of Hepatology*, 1999, 850-858, vol. 30.

Golkar, L., "Mastocytosis," *Lancet*, 1997, 1379-1385, vol. 349.

Hallek, M., "Interaction Of The Receptor Tyrosine Kinase p145$^{c\text{-kit}}$ With the p210$^{bcr/abl}$ Kinase In Myeloid Cells," *British Jounral of Haematology*, 1996, 5-16, vol. 94.

Hamel, W., "The Road Less Travelled: C-Kit And Stem Cell Factor," *Journal of Neuro-Oncology*, 1997, 327-333, vol. 35.

Hassan, H.T., "Stem Cell Factor As A Survival And Growth Factor In Human Normal And Malignant Hematopoiesis," *Acta Haematologica*, 1996, 257-262, vol. 95.

Hibi, K., "Coexpression Of The Stem Cell Factor And The C-Kit Genes In Small-Cell Lung Cancer," *Oncogene*, 1991, 2291-2296, vol. 6.

Hirota, S., "Gain-Of-Function Mutations Of C-Kit In Human Gastrointestinal Stromal Tumors," *Science*, 1998, 577-580, vol. 279.

Holgate, S., "Asthma: A Dynamic Disease Of Inflammation And Repair," *Ciba Foundation Symposium*, 1997, 5-34, vol. 206.

Iemura, A., "The C-Kit Ligand, Stem Cell Factor, Promotes Mast Cell Survival By Suppressing Apoptosis," *American Journal Of Pathology*, 1994, 321-328, vol. 144, No. 2.

Inoue, M. "Coexpression Of The C-Kit Receptor And The Stem Cell Factor In Gynecological Tumors," *Cancer Research*, 1994, 3049-3053, vol. 54.

Isozaki, K., "Deficiency Of C-Kit+ Cells In Patients With A Myopathic Form Of Chronic Idiopathic Intestinal Pseudo-Obstruction," *The American Journal of Gastroenterology*, 1997, 332-334, vol. 92, No. 2.

Izquierdo, M., "Differential Expression Of The C-Kit Proto-Oncogene In Germ Cell Tumours," *Journal of Pathology*, 1995, 253-258, vol. 177.

Jellinek, D., "Inhibition Of Receptor Binding By High-Affinity RNA Ligands To Vascular Endothelial Growth Factor," *Biochemistry*, 1994, 10450-10456, vol. 33.

Jones, R., "Biology And Treatment Of Chronic Myeloid Leukemia," *Current Opinion in Oncology*, 1997, 3-7, vol. 9.

Kendall, R., "Inhibition Of Vascular Endothelial Cell Growth Factor Activity By An Endogenously Encoded Soluble Receptor," *PNAS USA*, 1993, 10705-10709, vol. 90.

Kim, K., "Inhibition Of Vascular Endothelial Growth Factor-Induced Angiogenesis Suppresses Tumour Growth In Vivo," *Nature*, 1993, 841-844, vol. 362.

Kinashi, T., "Steel Factor And C-Kit Regulate Cell-Matrix Adhesion," *Blood*, 1994, 1033-1038, vol. 83, No. 4.

Kinsella, J.L., "Protein Kinase C Regulates Endothelial Cell Tube Formation On Basement Membrane Matrix, Matrigel," *Experimental Cell Research*, 1992, 56-62, vol. 199.

Kissel, H., "Point Mutation In Kit Receptor Tyrosine Kinase Reveals Essential Roles For Kit Signaling In Spermatogenesis and Oogenesis Without Affecting Other Kit Responses," *The EMBO Journal*, 2000, 1312-1326, vol. 19, No. 6.

Kitamura, Y., "Regulation of Development, Survival And Neoplastic Growth of Mast Cells Through The C-Kit Receptor," *International Archive of Allergy and Immunology*, 1995, 54-56, vol. 107.

Kohler, G., "Continuous Cultures Of Fused Cells Secreting Antibody of Predefined Speficity," *Nature*, 1975, 495-497, vol. 256.

Kondoh, G., "An In Vivo Model For Receptor Tyrosine Kinase Autocrine/Paracrine Activation: Auto-Stimulated KIT Receptor Acts As A Tumor Promoting Factor In Papillomavirus-Induced Tumorigenesis," *Oncogene*, 1995, 341-347, vol. 10.

Kondoh, G., "Establishment And Further Characterization Of A Line Of Transgenic Mice Showing Testicular Tumorigenesis At 100% Incidence," *The Journal Of Urology*, 1994, 2151-2154, vol. 152.

Kondoh, G., "Very High Incidence Of Germ Cell Tumorigenesis (Seminomagenesis) In Human Papillomavirus Type 16 Transgenic Mice," *Journal of Virology*, 1991, 3335-3339, vol. 65, No. 6.

Korc, M., "Overexpression Of The Epidermal Growth Factor Receptor In Human Pancreatic Cancer Is Associated With Concomitant Increases In The Levels Of Epidermal Growth Factor And Transforming Growth Factor Alpha," *Journal of Clinical Investigation*, 1992, 1352-1360, vol. 90.

Kristt, D., "Receptor Tyrosine Kinase Expression In Astrocytic Lesions: Similar Features In Gliosis And Glioma," *Neurosurgery*, 1993, 106-115, vol. 33, No. 1.

Krueger, N., "A Human Transmembrane Protein-Tyrosine-Phosphatase, PTPζ, Is Expressed In Brain And Has An N-Terminal Receptor Domain Homologous To Carbonic Anhyrases," *PNAS USA*, 1992, 7417-7421, vol. 89.

Kumabe, T., "Amplification Of α-Platelet-Derived Growth Factor Receptor Gene Lacking An Exon Coding For A Portion Of The Extracellular Region In A Primary Brain Tumor Of Glial Origin," *Oncogene*, 1992, 627-633, vol. 7.

Kunisada, T., "Murine Cutaneous Mastocytosis And Epidermal Melanocytosis Induced By Keratinocyte Expression Of Transgenic Stem Cell Factor," *Journal of Experimental Medicine*, 1998, 1565-1573, vol. 187, No. 10.

Lahm, H., "Interleukin 4 Down-Regulates Expression of C-Kit And Autocrine Stem Cell Factor In Human Colorectal Carcinoma Cells," *Cell Growth & Differentiation*, 1995, 1111-1118, vol. 6.

Lee, B., "Intracellular Of Membrane-Anchored V-Sis Protein Abrogates Autocrine Signal Transduction," *Journal of Cell Biology*, 1992, 1057-1070, vol. 118, No. 5.

Lee, J., "HLA-DR-Triggered Inhibition Of Hemopoiesis Involves Fas/Fas Ligand Interactions And Is Prevented By C-Kit Ligand[1]," *The Journal of Immunology*, 1997, 3211-3219, vol. 159.

Li, Q., "Abrogation of C-Kit/Steel Factor-Dependent Tumorigenesis By Kinase Defective Mutants Of The C-Kit Receptor: C-Kit Kinase Defective Mutants As Candidate Tools For Cancer Gene Therapy," *Cancer Research*, 1996, 4343-4346, vol. 56.

London, C.A., "Expression Of Stem Cell Factor Receptor (C-Kit) By The Malignant Mast Cells From Spontaneous Canine Mast Cell Tumours," *Journal of Comparative Pathology*, 1996, 399-414, vol. 115.

Longley, B., "Chymase Cleavage Of Stem Cell Factor Yields A Bioactive, Soluble Product," *PNAS USA*, 1997, 9017-9021, vol. 94.

Longley, B., "Somatic C-Kit Activating Mutation In Urticaria Pigmentosa And Aggressive Mastocytosis: Establishment Of Clonality In A Human Mast Cell Neoplasm," *Nature Genetics*, 1996, 312-314, vol. 12.

Loveland, K., "Stem Cell Factor And C-Kit In The Mammalian Testis: Lessons Originating From Mother Nature's Gene Knockouts," *Journal of Endocrinology*, 1997, 337-344, vol. 153.

Lukacs, N., "Stem Cell Factor (C-Kit Ligand) Influences Eosinophil Recruitment And Histamine Levels In Allergic Airway Inflammation," *The Journal Of Immunology*, 1996, 3945-3951, vol. 156.

Lyman, S., "C-Kit Ligand And Flt3 Ligand: Stem/Progenitor Cell Factors With Overlapping Yet Distinct Activities," *Blood*, 1998, 1101-1134, vol. 91, No. 4.

Ma, Y., "Clustering Of Activating Mutations In C-Kit's Juxtamembrane Coding Region In Canine Mast Cell Neoplasms," *Journal of Investigative Dermatology*, 1999, 165-170, vol. 112, No. 2.

Ma, Y., "Inhibition Of Spontaneous Receptor Phosphorylation By Residues In A Putative α-Helix In The KIT Intracellular Juxtamembrane Region," *The Journal of Biological Chemistry*, 1999, 13399-13402, vol. 274, No. 19.

Mariani, M., "Inhibition of Angiogenesis By FCE 26806, A Potent Tyrosine Kinase Inhibitor," *Proceedings of the American Association For Cancer Research*, 1994, 2268, vol. 35.

Mauduit, C., "Stem Cell Factor/C-Kit System In Spermatogenesis," *Human Reproduction Update*, 1999, 535-545, vol. 5, No. 5.

Mekori, Y., "The Role Of C-Kit And Its Ligand, Stem Cell Factor, In Mast Cell Apoptosis," *International Archives of Allergy and Immunology*, 1995, 136-138, vol. 107.

Mekori, Y., "Transforming Growth Factor-β Prevents Stem Cell Factor-Mediated Rescue Of Mast Cells From Apoptosis After IL-3 Deprivation," *The Journal of Immunology*, 1994, 2194-2203, vol. 153.

Meltzer, E.O., "The Pharmacological Basis For The Treatment Of Perennial Allergic Rhinitis And Non-Allergic Rhinitis With Topical Corticosteroids," *Allergy*, 1997, 33-40, vol. 52.

Metcalf, D., "Lineage Commitment In The Progeny Of Murine Hematopoietic Preprogenitor Cells: Influence Of Thrombopoietin And Interleukin 5," *PNAS USA*, 1998, 6408-6412, vol. 95.

Metcalfe, D., "Mast Cells," *Physiological Reviews*, 1997, 1033-1079, vol. 77, No. 4.

Metcalfe, D., "Classification And Diagnosis Of Mastocytosis: Current Status," *Journal of Investigative Dermatology*, 1991, 2S-4S, vol. 96.

Murty, V., "A Genetic Perspective Of Male Germ Cell Tumors," *Seminars In Oncology*, 1998, 133-144, vol. 25, No. 2.

Naclerio, R., "Rhinitis And Inhalant Allergens," *JAMA*, 1997, 1842-1848, vol. 278, No. 22.

Nagata, H., "Elevated Expression Of The Proto-Oncogene C-Kit In Patients With Mastocytosis," *Leukemia*, 1998, 175-181, vol. 12.

Natali, P.G., "Progression Of Human Cutaneous Melanoma Is Associated With Loss Of Expression Of C-Kit Proto-Oncogene Receptor," *International Journal of Cancer*, 1992, 197-201, vol. 52.

Ohta, H., "Regulation Of Proliferation And Differentiation In Spermatogonial Stem Cells: The Role of C-Kit And Its Ligand SCF," *Development*, 2000, 2125-2131, vol. 127.

Okayama, Y., "Activation Of Eosinophils With Cytokines Produced By Lung Mast Cells," *International Archives of Allergy and Immunology*, 1997, 75-77, vol. 114.

Okayama, Y., "Human Lung Mast Cells Are Enriched In The Capacity To Produce Granulocyte-Macrophage Colony-Stimulating Factor In Response To IgE-Dependent Stimulation," *European Journal of Immunology*, 1998, 708-715, vol. 28.

Pardo, J., "Mast Cells In Chronic Rejection Of Human Renal Allografts," *Virchows Archives*, 2000, 167-172, vol. 437.

Parrott, J., "Kit-Ligand/Stem Cell Factor Induces Primordial Follicle Development And Initiates Folliculogenesis," *Endocrinology*, 1999, 4262-4271, vol. 140, No. 9.

Pignon, J.-M., "C-Kit Mutations And Mast Cell Disorders A Model of Activating Mutations of Growth Factor Receptors," *Hematology Cell Therapy*, 1997, 114-116, vol. 39.

Qiu, F., "Primary Structure Of C-Kit: Relationship With The CSF-1/PDGF Receptor Kinase Family—Oncogenic Activation of V-Kit Involves Deletion of Extracellular Domain And C Terminus," *The EMBO Journal*, 1988, 1003-1011, vol. 7, No. 4.

Rajpert-De Meyts, E., "Expression Of The C-Kit Protein Product In Carcinoma-In-Situ And Invasive Testicular Germ Cell Tumours," *International Journal of Andrology*, 1994, 85-92, vol. 17.

Ricotti, E., "C-Kit Is Expressed In Soft Tissue Sarcoma of Neuroectodermic Origin And Its Ligand Prevents Apoptosis of Neoplastic Cells," *Blood*, 1998, 2397-2405, vol. 91, No. 7.

Ryan, J.J., "Rapid Communication, Role For The Stem Cell Factor/Kit Complex In Schwann Cell Neoplasia And Mast Cell Proliferation Associated With Neurofibromatosis," *Journal of Neuroscience Research*, 1994, 415-432, vol. 37.

Saito, H., "Molecular Characterization of Protein Tyrosine Phosphatases," *Cell Growth & Differentiation*, 1991, 59-65, vol. 2.

Sandlow, J., "Expression Of C-Kit And Its Ligand, Stem Cell Factor, In Normal And Subfertile Human Testicular Tissue," *Journal of Andrology*, 1996, 403-408, vol. 17, No. 4.

Sawada, K., "Role Of Cytokines In Leukemic Type Growth of Myelodysplastic CD34+ Cells," *Blood*, 1996, 319-327, vol. 88, No. 1.

Sawai, N., "Aberrant Growth of Granulocyte-Macrophage Progenitors In Juvenile Chronic Myelogenous Leukemia In Serum-Free Culture," *Experimental Hematology*, 1996, 116-122, vol. 24.

Scheffner, M., "The E6 Oncoprotein Encoded By Human Papillomavirus Types 16 and 18 Promotes The Degradation of p53," *Cell*, 1990, 1129-1136, vol. 63.

Schlessinger, J., "Growth Factor Signaling By Receptor Tyrosine Kinases," *Neuron*, 1992, 383-391, vol. 9.

Schuchter, L., "Successful Treatment of Murine Melanoma With Bryostatin 1[1]," *Cancer Research*, 1991, 682-687, vol. 51.

Secor, V., "Mast Cells Are Essential For Early Onset And Severe Disease In A Murine Model Of Multiple Sclerosis," *The Journal of Experimental Medicine*, 2000, 813-821, vol. 191, No. 5.

Slamon, D., "Studies of The HER-2/Neu Proto-Oncogene In Human Breast And Ovarian Cancer," *Science*, 1989, 707-712, vol. 244.

Sperling, C., "Expression Of The Stem Cell Factor Receptor C-Kit (CD117) In Acute Leukemias," *Haematologica*, 1997, 617-621, vol. 82.

Stanulla, M., "Coexpression Of Stem Cell Factor And Its Receptor C-Kit In Human Malignant Glioma Cell Lines," *Acta Neuropathology*, 1995, 158-165, vol. 89.

Strohmeyer, T., "Expression Of The C-Kit Proto-Oncogene And Its Ligand Stem Cell Factor (SCF) In Normal And Malignant Human Testicular Tissue," *The Journal of Urology*, 1995, 511-515, vol. 153.

Strohmeyer, T., "Expression Of The HST-1 And C-Kit Protooncogenes In Human Testicular Germ Cell Tumors," *Cancer Research*, 1991, 1811-1816, vol. 51.

Tada, M., "Analysis Of Cytokine Receptor Messenger RNA Expression In Human Glioblastoma Cells And Normal Astrocytes By Reverse-Transcription Polymerase Chain Reaction," *Journal of Neurosurgery*, 1994, 1063-1073, vol. 80.

Takano, S., "Inhibition Of Angiogenesis By a Novel Diaminoanthraquinone That Inhibits Protein Kinase C.," *Molecular Biology Of The Cell*, 1993, 358a, vol. 4.

Thomas, L., "The Eosinophil And Its Role In Asthma," *General Pharmacology*, 1996, 593-597, vol. 27, No. 4.

Torp, S., "Expression Of The Epidermal Growth Factor Receptor Gene In Human Brain Metastases," *APMIS*, 1992, 713-719, vol. 100.

Toyota, M., "Expression Of C-Kit And Kit Ligand In Human Colon Carcinoma Cells," *Tumor Biology*, 1993, 295-302, vol. 14.

Tsujimura, T., "Ligand-Independent Activation Of C-Kit Receptor Tyrosine Kinase In A Murine Mastocytoma Cell Line P-815 Generated By A Point Mutation," *Blood*, 1994, 2619-2626, vol. 83, No. 9.

Tsujimura, T., "Role of C-Kit Receptor Tyrosine Kinase In The Development, Survival And Neoplastic Transformation Of Mast Cells," *Pathology International*, 1996, 933-938, vol. 46.

Tsujimura, T., "Substitution Of An Aspartic Acid Results In Constitutive Activation of C-Kit Receptor Tyrosine Kinase In A Rat Tumor Mast Cell Line RBL-2H3," *International Archives of Allergy and Immunology*, 1995, 377-385, vol. 106.

Turner, A., "Nonhematopoietic Tumor Cell Lines Express Stem Cell Factor And Display C-Kit Receptors," *Blood*, 1992, 374-381, vol. 80, No. 2.

Tuzi, N.L., "Expression Of Growth Factor Receptors In Human Brain Tumours," *British Journal of Cancer*, 1991, 227-233, vol. 63.

Valent, P., "Biology, Classification And Treatment Of Human Mastocytosis," *Wien Klin Wochenschr*, 1996, 385-397, vol. 183, No. 123.

Verfaillie, C.M., "Chronic Myelogenous Leukemia: Too Much Or Too Little Growth, Or Both?" *Leukemia*, 1998, 136-138, vol. 12.

Vliagoftis, H., "The Protooncogene C-Kit And C-Kit Ligand In Human Disease," *Journal of Allergy and Clinical Immunology*, 1997, 435-440, vol. 100, No. 4.

Werness, B., "Association Of Human Papillomavirus Types 16 And 18 E6 Proteins With p53," *Science*, 1990, 76-79, vol. 248.

Wright, P., "Inhibition Of Angiogenesis In Vitro And In Ovo With An Inhibitor Of Cellular Protein Kinases, MDL 27032," *Journal of Cellular Physiology*, 1992, 448-457, vol. 152.

Yamaguchi, Y., "Expression Of The C-Kit Proto-Oncogene In Rat Hepatic Allografts During Acute Rejection," *Hepatology*, 1999, 133-139, vol. 29.

Yarden, Y., "Human Proto-Oncogene C-Kit: A New Cell Surface Receptor Tyrosine Kinase For An Unidentified Ligand," *The EMBO Journal*, 1987, 3341-3351, vol. 6, No. 11.

Yee, N., "Role of Kit-Ligand In Proliferation And Suppression Of Apoptosis In Mast Cells: Basis For Radiosensitivity Of White Spotting And Steel Mutant Mice," *Journal of Experimental Medicine*, 1994, 1777-1787, vol. 179.

Yuan, B., "Human Peripheral Blood Eosinophils Express A Functional C-Kit Receptor For Stem Cell Factor That Stimulates Very Late Antigen 4 (VLA-4)-Mediated Cell Adhesion To Fibronectin And Vascular Cell Adhesion Molecule 1 (VCAM-1)," *Journal of Experimental Medicine*, 1997, 313-323, vol. 186, No. 2.

Anderson, D., et al, Molecular Cloning of Mast Cell Growth Factor, a Hematopoietin That Is Active in Both Membrane Bound and Soluble Forms, *Cell*, 1990, 235-243, vol. 63.

Askenase, P., et al., "Defective Elicitation of Delayed-Type Hypersensitivity in W/W$^v$ and S1/S1$^d$ Mast Cell-Deficient Mice[1]," *The Journal of Immunology*, 1983, 2687-2693, vol. 131, No. 6.

Bradl, M., et al., "Clonal Coat Color Variation Due to a Transforming Gene Expressed in Melanocytes of Transgenic Mice," *Proceedings of the National Academy of Sciences*, 1991, 6447-6451, vol. 88.

Costa, J., et al., "Recombinant Human Stem Cell Factor (Kit Ligand) Promotes Human Mast Cell and Melanocyte Hyperplasia and Functional Activation in Vivo," *Journal of Experimental Medicine*, 1996, 2681-2686, vol. 183.

Devinney, R., et al., "Establishment of Two Dog Mastocytoma Cell Lines in Continuous Culture," *American Journal of Respiratory Cell and Molecular Biology*, 1990, 413-420, vol. 3, No. 5.

Dunn, T., et al., "A Transplantable Mast-Cell Neoplasm in the Mouse," *Journal of the National Cancer Institute*, 1957, 587-601, vol. 18, No. 4.

Funasaka, Y., et al., "c-Kit-Kinase Induces a Cascade of Protein Tyrosine Phosphorylation in normal Human Melanocytes in Response to Mast Cell Growth Factor and Stimulates Mitogen-Activated Protein Kinase But is Down-Regulated in Melanomas," *Molecular Biology of the Cell*, 1992, 197-209, vol. 3.

Furitsu, T., et al., "Identification of Mutations in the Coding Sequence of the Proto-Oncogene c-kit in a Human Mast Cell Leukemia Cell Line Causing Ligand-independent Activation of c-kit Product," *Journal of Clinical Investigation*, 1993, 1736-1744, vol. 92.

Grichnik, J., et al., "Human Recominant Stem-cell Factor Induces Melanocytic Hyperplasia in Susceptible Patients," *Journal of the American Academy of Dermatology*, 1995, 577-583, vol. 33, No. 4.

Hamann, K., et al., "Expression of Stem Cell Factor in Cutaneous Mastocytosis," *British Journal of Dermatology*, 1995, 203-208, vol. 133.

Harrist, T., et al., "Recombinant Human Stem Cell Factor(SCF) (c-kit Ligand) Promotes Melanocyte Hyperplasia and Activation In Vivo," *Laboratory Investigation*, 1995, 48A, vol. 72, No. 1.

Hirobe, T., "Histochemical Survey of the Distribution of the Epidermal Melanoblasts and Melanocytes in the Mouse During Fetal and Postnatal Periods," *The Anatomical Record*, 1984, 589-594, vol. 208.

Lazarus, S., et al., "Isolated Canine Mastocytoma Cells: Propagation and Characterization of Two Cell Lines," *American Journal of Physiology*, 1986, 935-944, vol. 251, No. 6.

Longley, JR., B., et al., "Altered Metabolism of Mast-Cell Growth Factor (c-kit Ligand) in Cutaneous Mastocytosis," *The New England Journal of Medicine*, 1993, 1302-1307, vol. 328, No. 18.

Longley, J., et al., "The Mast Cell and Mast Cell Disease," *Journal of the American Academy of Dermatology*, 1995, 545-561, vol. 32, No. 4.

Longley, B., et al., "Somatic c-KIT Activating Mutation in Urticaria Pigmentosa and Aggressive Mastocytosis: Establishment of Clonality in a Human Mast Cell Neoplasm," *Nature Genetics*, 1996, 312-314, vol. 12, No. 3.

Lu, H., et al., "Amino Acid Sequence and Post-Translational Modification of Stem Cell Factor Isolated from Buffalo Ret Liver Cell-Conditioned Medium," *The Journal of Biological Chemistry*, 1991, 8102-8107, vol. 266, No. 13.

Ma, Y., et al., "Indolinone Derivatives Inhibit Constitutively Activated KIT Mutants and Kill Neoplastic Mast Cells," *The Journal of Investigative Dermatology*, 2000, 392-394, vol. 114, No. 2.

Martin, F., et al., "Primary Structure and Functional Expression of Rat and Human Stem Cell Factor DNAs," *Cell*, 1990, 203-211, vol. 63.

Mekori, Y., et al., "Undiminished Immunologic Tolerance to Contact Sensitivity in Mast Cell-Deficient W/W$^v$ and S1/S1$^d$ Mice[1]," *The Journal of Immunology*, 1985, 879-885, vol. 135, No. 2.

Mohammadi, M., et al., "Structures of the Tyrosine Kinase Domain of Fibroblast Growth Factor Receptor in complex with Inhibitors," *Science*, 1997, 995-960, vol. 276, No. 4314.

Nishikawa, S., et al., "In Utero Manipulation of Coat Color Formation by a Monoclonal Anti-c-KIT Antibody: Two Distinct Waves of c-KIT- Dependency during Melanocyte Development," *The EMBO Journal*, 1991, 2111-2118, vol. 10, No. 8.

Okura, M., et al., "Effects of Monoclonal Anti-C-KIT Antibody (AKC2) on Melanocytes in Newborn Mice," *The Journal of Investigative Dermatology*, 1995, 322-328, vol. 105, No. 3.

Piao, X., et al., "Oncogenic Mutation in the Kit Receptor Tyrosine Kinase Alters Substrate Specificity and Induces Degradation of the Protein Tyrosine Phosphatase SHP-1," *Proceedings of the National Academy of Science of the United States of America*, 1996, 14665-14669, vol. 93.

Qiu, F., et al., "Primary Structure of c-KIT: Relationship with the CSF-1/PDGF Receptor Kinase Family—Oncogenic Activation of v-KIT Involves Deletion of Extracellular Domain and C Terminus," *The EMBO Journal*, 1988, 1003-1011, vol. 7, No. 4.

Sun, L., et al., "Synthesis and Biological Evaluations of 3-Substituted Indolin-2-ones: A Novel Class of Tyrosine Kinases," *Journal of Medicinal Chemistry*, 1998, 2588-2603, vol. 41.

Thomas, W., et al., "Delayed Hypersensitivity in Mast-Cell-Deficient Mice," *The Journal of Immunology*, 1983, 2565-2567, vol. 130, No. 6.

Tsai, M., et al., "The Rat c-KIT Ligand, Stem Cell Factor, Induces the Development of Connective Tissue-Type and Mucosal Mast Cells In Vivo. Analysis by Anatomical Distribution, Histochemistry, and Protease Phenotype," *The Journal of Experimental Medicine*, 1991, 125-131, vol. 174, No. 1.

Tsujimura, T., et al., "Ligand-Independent Activation of c-KIT Receptor Tyrosine Kinase in a Murine Mastocytoma Cell Line P-815 Generated by a Point Mutation," *Blood*, 1994, 2619-2626, vol. 83.

Vassar, R., et al., "Tissue-Specific and Differentiation-Specific Expression of a Human K14 Keratin Gene in Transgenic Mice," *Proceedings of the National Academy of Sciences*, 1989, 1563-1567, vol. 86, No. 5.

Weiss, R., et al, "Human Dermal Endothelial Cells Express Membrane-Associated Mast Cell Growth Factor," *The Journal of Investigative Dermatology*, 1995, 101-106, vol. 104, No. 1.

Williams, D., et al., "Identification of a Ligand for the c-KIT Proto-Oncogene," *Cell*, 1990, 167-174, vol. 63, No. 1.

Yarden, Y., et al., "Human Proto-Oncogene c-KIT: A New Cell Surface Receptor Tyrosine Kinase for an Unidentified Ligand," *The EMBO Journal*, 1987, 3341-3351, vol. 6, No. 11.

Yoshida, H., et al., "Distinct Stages of Melanocyte Differentiation Revealed by Analysis of Nonuniform Pigmentation Patterns," *Development*, 1996, 1207-1214, vol. 122, No. 4.

Yoshida, H., et al., "Neural and Skin Cell-Specific Expression Pattern Conferred by Steel Factor Regulatory Sequence in Transgenic Mice," *Developmental Dynamics*, 1996, 222-232, vol. 207, No. 2.

Zsebo, K., et al., "Stem Cell Factor is Encoded at the S1 Locus of the Mouse and is the Ligand of the c-KIT Tyrosine Kinase Receptor," *Cell*, 1990, 213-224, vol. 63, No. 1.

\* cited by examiner

CSF-1r/ c-fms
SCFr/ c-kit
flt-3/flk-2

Figure 2

| Compound No. | c-kit Kinase IC$_{50}$ (nM) |
|---|---|
| Compound Thirteen | 240 |
| Compound One | 4.3 |
| Compound Nine | 540 |
| Compound Eleven | 770 |
| Compound Two | 88 |
| Compound Ten | 0.14 |
| Compound Seven | 0.00042 |
| Compound Five | 45 |
| Compound Three | 160 |
| Compound Four | 37 |
| Compound Twelve | 15 |
| Compound Six | 2.5 |
| Compound Eight | 52 |

METHODS OF MODULATING C-KIT TYROSINE PROTEIN KINASE FUNCTION WITH INDOLINONE COMPOUNDS

The entire disclosure of U.S. parent application Ser. No. 10/600,868 filed Jun. 23, 2003 is fully incorporated herein by reference thereto.

This application claims priority to U.S. Ser. No. 60/171,693, filed Dec. 22, 1999, the entirety of which is hereby incorporated by reference.

FIELD OF THE INVENTION

The present invention relates to methods, compounds, and compositions for inhibiting cell proliferative disorders. The invention is particularly useful for inhibiting cell proliferative disorders characterized by overactivity and/or inappropriate activity of a c-kit kinase.

BACKGROUND OF THE INVENTION

The following description of the background of the invention is provided to aid in understanding the invention, but is not admitted to describe or constitute prior art to the invention.

Kit signaling is critical for fetal gonadal development, and continues to play a role in adult fertility (Mauduit et al. (1999) Human Reproduction Update 5:535–545). Spermatogenesis is inhibited in the absence of SCF (Ohta et al. (2000) Development 127:2125–2131) or the ability of Kit to signal through the PI3 kinase pathway (Blume-Jensen et al. (2000) Nature Genetics 24:157–162; Kissel et al. (2000) EMBO Journal 19:1312–1326). Kit expression has also been observed to be lower in sub-fertile testes than in normal testicular tissue (Feng et al. (1999) Fertility & Sterility 71:85–89). Kit signaling is also important for oogenesis and folliculogenesis (Parrott & Skinner (1999) Endocrinology 140:4262–4271; Driancourt et al. (2000) Reviews of Reproduction 5:143–152). These observations suggest that Kit kinase inhibitors would reduce both male and female fertility.

As a key mediator of mast cell function, Kit may play a role in pathologies associated with mast cells. For example, mast cells have been associated with interstitial fibrosis in chronic rejection of human renal allografts (Pardo et al. (2000) Virchows Archiv 437:167–172). Mast cells have also been implicated in liver allograft rejection (Yamaguchi et al. (1999) Hepatology 29:133–139) and in liver fibrosis, where hepatic stellate cells produce the SCF that recruits the mast cells (Gaca et al. (1999) J. Hepatology 30:850–858). These observations suggest the Kit kinase inhibitors may help prevent organ rejection and fibrosis.

Mast cells have also been implicated in the pathology of multiple sclerosis (Secor et al. (2000) J. Experimental Medicine 191:813–822) and ischemia-reperfusion injury (Andoh et al. (1999) Clinical & Experimental Immunology 116: 90–93) in experimental models using mice with mutant Kit receptors that are deficient in mast cells. In both cases, the pathology of the disease was significantly attenuated relative to mice with normal Kit and mast cells populations. Thus, the role of mast cells in these diseases suggests that Kit kinase inhibitors might be useful therapeutics.

Cellular signal transduction is a fundamental mechanism whereby extracellular stimuli are relayed to the interior of cells and subsequently regulate diverse cellular processes. One of the key biochemical mechanisms of signal transduction involves the reversible phosphorylation of proteins. Phosphorylation of polypeptides regulates the activity of mature proteins by altering their structure and function. Phosphate most often resides on the hydroxyl moiety (—OH) of serine, threonine, or tyrosine amino acids in proteins.

Enzymes that mediate phosphorylation of cellular effectors generally fall into two classes. The first class consists of protein kinases which transfer a phosphate moiety from adenosine triphosphate to protein substrates. The second class consists of protein phosphatases which hydrolyze phosphate moieties from phosphoryl protein substrates. The converse functions of protein kinases and protein phosphatases balance and regulate the flow of signals in signal transduction processes.

Protein kinases and protein phosphatases are generally divided into two groups: receptor and non-receptor type proteins. Most receptor-type protein tyrosine phosphatases contain two conserved catalytic domains, each of which encompasses a segment of 240 amino acid residues. Saito, et al., 1991, Cell Growth and Diff 2:59–65. Receptor protein tyrosine phosphatases can be subclassified further based upon the amino acid sequence diversity of their extracellular domains. Saito, et al., supra; Krueger, et al., 1992, Proc. Natl. Acad. Sci. USA 89:7417–7421.

Protein kinases and protein phosphatases are also typically divided into three classes based upon the amino acids they act upon. Some catalyze the addition or hydrolysis of phosphate on serine or threonine only, some catalyze the addition or hydrolysis of phosphate on tyrosine only, and some catalyze the addition or hydrolysis of phosphate on serine, threonine, and tyrosine.

Tyrosine kinases can regulate the catalytic activity of other protein kinases involved in cell proliferation. Protein kinases with inappropriate activity are also involved in some types of cancer. Abnormally elevated levels of cell proliferation are associated with receptor and non-receptor protein kinases with unregulated activity.

In addition to their role in cellular proliferation, protein kinases are thought to be involved in cellular differentiation processes. Cell differentiation occurs in some cells upon nerve growth factor (NGF) or epidermal growth factor (EGF) stimulation. Cellular differentiation is characterized by rapid membrane ruffling, cell flattening, and increases in cell adhesion. (Chao, 1992, Cell 68:995–997).

In an effort to discover novel treatments for cancer and other diseases, biomedical researchers and chemists have designed, synthesized, and tested molecules that inhibit the function of protein kinases. Some small organic molecules form a class of compounds that modulate the function of protein kinases. Examples of molecules that have been reported to inhibit the function of protein kinases are bis-monocyclic, bicyclic or heterocyclic aryl compounds (PCT WO 92/20642), vinylene-azaindole derivatives (PCT WO 94/14808), 1-cyclopropyl-4-pyridyl-quinolones (U.S. Pat. No. 5,330,992), styryl compounds (by Levitzki, et al., U.S. Pat. No. 5,217,999, and entitled "Styryl Compounds which Inhibit EGF Receptor Protein Tyrosine Kinase, styryl-substituted pyridyl compounds (U.S. Pat. No. 5,302,606), certain quinazoline derivatives (EP Application No. 0 566 266 A1), seleoindoles and selenides (PCT WO 94/03427), tricyclic polyhydroxylic compounds (PCT WO 92/21660), and benzylphosphonic acid compounds (PCT WO 91/15495).

The compounds that can traverse cell membranes and are resistant to acid hydrolysis are potentially advantageous therapeutics as they can become highly bioavailable after being administered orally to patients. However, many of these protein kinase inhibitors only weakly inhibit the function of protein kinases. In addition, many inhibit a variety of protein kinases and will therefore cause multiple side-effects as therapeutics for diseases.

Despite the significant progress that has been made in developing compounds for the treatment of cancer, there remains a need in the art to identify the particular structures and substitution patterns that form the compounds capable of modulating the function of particular protein kinases.

SUMMARY OF THE INVENTION

The present invention is directed in part towards indolinone compounds and methods of modulating the function of protein kinases with these compounds. In addition, the invention describes methods of treating and preventing protein kinase-related abnormal conditions in organisms with a compound identified by the methods described herein. Furthermore, the invention pertains to pharmaceutical compositions containing compounds identified by methods of the invention.

The present invention features indolinone compounds that potently inhibit receptor protein kinases of the c-kit family and related products and methods. Other inhibitors and/or activators of c-kit protein kinases can be obtained by adding chemical substituents to an unsubstituted indolinone compound (See Formulas I and II, below). The compounds of the invention provide therapeutics and/or prophylactics for diseases associated with one or more functional c-kit protein kinases. Certain types of cancer fall into this class of diseases, along with certain immune disorders associated with the over-production or over-stimulation of mast cells. The compounds can be modified such that they are specific to their target or targets and will subsequently cause few side effects. These properties are significant improvements over the currently utilized cancer therapeutics that cause multiple side effects and deleteriously weaken patients.

The compounds, compositions, and methods of the invention will minimize or obliterate certain types of solid tumors and leukemias by inhibiting the activity of the c-kit receptor protein kinases, or will at least modulate or inhibit tumor growth and/or metastases. Certain types of cancer, such as Small Cell Lung Cancer (SCLC), express both the c-kit receptor protein kinase and Stem Cell Factor (SCF), a c-kit ligand.

While a precise understanding of the mechanism by which compounds inhibit phosphotyrosine kinases (PTKs) (e.g., the c-kit receptor kinase, a transmembrane tyrosine kinase growth factor receptor) is not required in order to practice the present invention, the compounds are believed to interact with the amino acids of the PTKs' catalytic region. PTKs typically possess a bi-lobate structure, and ATP appears to bind in the cleft between the two lobes in a region where the amino acids are conserved among PTKs; inhibitors of PTKs are believed to bind to the PTKs through non-covalent interactions such as hydrogen bonding, Van der Waals interactions, hydrophobic interactions, and ionic bonding, in the same general region that ATP binds to the PTKs. More specifically, it is thought that the oxindole component (See Formula III, below) of the compounds of the present invention binds in the same general space occupied by the adenine ring of ATP. Specificity of a PTK inhibitor for a particular PTK may be conferred by interactions between the constituents around the oxindole core with amino acid domains specific to individual PKs. Thus, different substituents may contribute to preferential binding to particular PKs. The ability to select those compounds active at different ATP binding sites makes them useful in targeting any protein with such a site, including not only protein tyrosine kinases, but also serine/threonine kinases. Thus, such compounds have utility for in vitro assays on such proteins and for in vivo therapeutic effect through such proteins. For example, as mentioned above, certain types of cancer express both the c-kit receptor protein kinase and Stem Cell Factor (SCF) and this pairing could constitute an autocrine loop stimulating the growth of these cancerous cells. Therefore, inhibition of the c-kit protein kinase could disrupt this autocrine loop and thereby retard tumor growth and/or obliterate tumors via normal mechanisms of apoptosis.

Thus, in a first aspect, the invention provides a method for treating or preventing an abnormal condition in an organism. The abnormal condition is associated with an aberration in a signal transduction pathway mediated by an interaction between a c-kit kinase and a natural binding partner. The method involves administering to the organism a therapeutically effective amount of an indolinone compound. The indolinone compound modulates the interaction between the c-kit kinase and a natural binding partner. Therefore, promoting or disrupting (preferably disrupting) this interaction is predicted to have therapeutic benefits to a given population of patients in need of such treatment. In a preferred embodiment, the amount of signaling through c-kit kinase is abnormal, and the compound promotes or disrupts the signaling.

The term "treating" refers to having a therapeutic effect and at least partially alleviating or abrogating an abnormal condition in the organism. The term "treating" preferably refers to ameliorating a symptom of the abnormal condition in a group of patients to whom the indolinone is administered relative to a control group that does not receive the indolinone. The effect of the treatment can be monitored by measuring a change or an absence of a change in cell phenotype, a change or an absence of a change in cell proliferation, a change or an absence of a change in the catalytic activity of this c-kit protein kinase, and a change or an absence of a change in the interaction between this protein kinase and a natural binding partner. The term "treating" or "treatment" does not necessarily mean total cure. Any alleviation of any undesired symptom of the disease to any extent or the slowing down of the progress of the disease can be considered treatment. Furthermore, treatment may include acts which may worsen the patient's overall feeling of well being or appearance. For example, the administration of chemotherapy in cancer patients which may leave the patients feeling "sicker" is still considered treatment.

The term "catalytic activity" used above, in the context of the invention, defines the rate at which a protein kinase phosphorylates a substrate. Catalytic activity can be measured, for example, by determining the amount of a substrate converted to a product as a function of time. Phosphorylation of a substrate occurs at the active site of a protein kinase. The active site is normally a cavity in which the substrate binds to the protein kinase and is phosphorylated.

The term "substrate" as used above and herein refers to a molecule phosphorylated by a protein kinase. The substrate is preferably a peptide and more preferably a protein.

The term "preventing" refers to decreasing the probability that an organism contracts or develops an abnormal condition. The term "preventing" preferably refers to reducing the percentage of individuals who develop the abnormal condition relative to a control group that does not undergo administration of an indolinone.

The term "abnormal condition" refers to a function in the cells or tissues of an organism that deviates from its normal functions in that organism. An abnormal condition can relate to cell proliferation, cell differentiation, or cell survival. Abnormal conditions include mastocytosis, the presence of one or more mast cell tumors, asthma, allergy-associated chronic rhinitis, small cell lung cancer, non-small cell lung cancer, acute myelocytic leukemia, acute lymphocytic leukemia, myelodysplastic syndrome, chronic myelogenous leukemia, colorectal carcinomas, gastric carcinomas, gastrointestinal stromal tumors, testicular cancers, glioblastomas, and astrocytomas. In a preferred embodiment, these abnormal conditions, such as mast cell tumors and mastocytosis, arise in non-human organisms and may thus be prevented or treated during the practice of veterinary medicine.

Abnormal cell survival conditions relate to conditions in which programmed cell death (apoptosis) pathways are activated or abrogated. A number of protein kinases are associated with the apoptosis pathways. Aberrations in the function of any one of the protein kinases could lead to cell immortality or premature cell death.

The term "function" as used in relation to a protein kinase above refers to the cellular role of a protein kinase, preferably a c-kit kinase. The protein kinase family includes members that regulate many steps in signaling cascades, including cascades controlling cell growth, migration, differentiation, gene expression, muscle contraction, glucose metabolism, cellular protein synthesis, and regulation of the cell cycle. The "function" of a membrane receptor kinase usually is to transduce a signal from outside a cell's membrane to the interior of a cell. To accomplish this it may perform one or all of these other functions: bind a ligand, dimerize to another membrane receptor kinase, phosphorylate other proteins within the cell, bind other proteins within the cell, and cause the localization of proteins within the cell.

The term "organism" relates to any living entity comprised of at least one cell. An organism can be as simple as one eukaryotic cell or as complex as a mammal. The organism is preferably a mammal, more preferably a human.

The term "mammal" refers preferably to such organisms as mice, rats, rabbits, guinea pigs, sheep, and goats, more preferably to cats, dogs, monkeys, and apes. In preferred embodiments, the abnormal condition associated with mammals may include mastocytosis, and the presence of one or more mast cell tumors.

The term "aberration," refers to a protein kinase, e.g., a c-kit kinase that is over- or under-expressed in an organism, mutated such that its catalytic activity is lower or higher than wild-type protein kinase activity, mutated such that it can no longer interact with a natural binding partner, no longer functions in an autocrine loop within the cell, is no longer modified by another protein kinase or protein phosphatase, or no longer interacts with a natural binding partner. Preferably, the aberration involves excessive or deficient signaling upon interaction with a natural binding partner.

The term "signal transduction pathway" refers to the molecules that propagate an extracellular signal through the cell membrane to become an intracellular signal. This signal can then stimulate a cellular response. The polypeptide molecules involved in signal transduction processes include receptor and non-receptor protein tyrosine kinases, receptor and non-receptor protein phosphatases, proteins containing SRC homology 2 and 3 domains, phosphotyrosine binding proteins (SRC homology 2 (SH2) and phosphotyrosine binding (PTB and PH) domain containing proteins), proline-rich binding proteins (SH3 domain containing proteins), GTPases, phosphodiesterases, phospholipases, prolyl isomerases, proteases, $Ca^{2+}$ binding proteins, cAMP binding proteins, guanyl cyclases, adenylyl cyclases, NO generating proteins, nucleotide exchange factors, and transcription factors.

The term "mediated" refers to involvement in the control or effect of the interaction between c-kit kinase and the natural binding partners on the aberration in the signal transduction pathway. Thus, the signal transduction pathway that has an aberration and is associated with the abnormal condition, contains a c-kit kinase in interaction with a natural binding partner.

The "interaction" of a c-kit kinase molecule is the binding of that c-kit kinase molecule to a natural binding partner or molecule within the cell or the phosphorylation by a c-kit kinase molecule of another protein-or molecule within the cell, or any other association of c-kit kinase within a cell. These interactions include non-covalent interactions such as hydrogen bonding, Van der Waals interactions, hydrophobic interactions, and ionic bonding.

The term "c-kit kinase" refers to a membrane receptor protein tyrosine kinase which is preferably activated upon binding Stem Cell Factor (SCF) to its extracellular domain (Yarden et al., 1987; Qiu et al., 1988). The receptor tyrosine kinase c-kit kinase contains 5 immunoglobulin-like motifs in the extracellular domain and a cytoplasmic "split" kinase domain, FIG. 1. The full length amino acid sequence of a c-kit kinase preferably is as set forth in Yarden, et al., 1987, *EMBO J.* 11:3341–3351; and Qiu, et al., 1988, *EMBO J.* 7:1003–1011, which are incorporated by reference herein in their entirety, including any drawings. Mutant versions of c-kit kinase are encompassed by the term "c-kit kinase" and include those that fall into two classes: (1) having a single amino acid substitution at codon 816 of the human c-kit kinase, or its equivalent position in other species (Ma et al., 1999, *J. Invest Dermatol* 112:165–170), and (2) those which have mutations involving the putative juxtamembrane z-helix of the protein (Ma, et al., 1999, *J. Biol Chem* 274: 13399–13402). Both of these publications are incorporated by reference herein in their entirety, including any drawings.

The term "natural binding partner" refers to a polypeptide or compound such as ATP that binds to a protein kinase in cells. Natural binding partners can play a role in propagating a signal in a protein kinase signal transduction process. A change in the interaction between a protein kinase and a natural binding partner can manifest itself as an increased or decreased probability that the interaction forms, or an increased or decreased concentration of the protein kinase/natural binding partner complex.

A "therapeutically effective" amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein. A "therapeutically effective amount," in reference to the treatment of a cancer refers to an amount sufficient to bring about one or more of the following results: reduce the size of the cancer, inhibit the metastasis of the cancer, inhibit the growth of the cancer, stop the growth of the cancer, relieve discomfort due to the cancer, or prolong the life of a patient inflicted with the cancer. A "therapeutically effective amount", in reference to the treatment of a cell proliferative disorder other than a cancer refers to an amount sufficient to bring about one or more of the following results: inhibit the growth of cells causing the disorder, relieve discomfort due to the disorder, or prolong the life of a patient suffering from the disorder.

The term "indolinone" is used as that term is commonly understood in the art and includes a large subclass of substituted or unsubstituted compounds that are capable of being synthesized from an aldehyde moiety and an oxindole moiety. In preferred embodiments, the indolinones included in the present method have the structures of Formulas I and II (see below), and more preferably are selected from Compounds One through Thirteen (see below).

Examples of representative indolinone compounds and the synthesis thereof, are set forth in the following applications: (1) PCT application No. U599/06468, filed Mar. 26,1999 by Fong, et.al. and entitled METHODS OF MODULATING TYROSINE PROTEIN KJNASE (2) U.S. Provisional Application No. 60/131,192, filed Apr. 26, 1999 by Tang,è/ al. and entitled DIARYL INDOLINONE COMPOUNDS AS KINASE INHIBITORS, U.S. application Ser. No. 09/283,657, filed Apr. 1, 1999 by Tang, et al., and entitled METHODS OF MODULATING TYROSINE PROTEIN KINASE FUNCTION WITH INDOLINONE COMPOUNDS, and (4) U.S. Pat. No. 5,792,783, issued Aug. 11, 1998 by Tang et al., entitled 3-HETEROARYL-2-MDOLI-NONE COMPOUNDS FOR THE TREATMENT OF DISEASE which are hereby incorporated by reference in their entirety including any drawings.

Preferably, the compounds used in the invention have a structure set forth in Formula I,

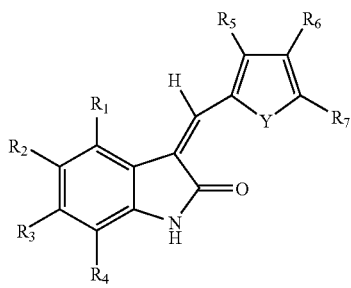

(I)

wherein (a) Y is selected from the group consisting of oxygen, sulfur and nitrogen substituted with a hydrogen;

(b) $R_1$, $R_2$, $R_3$, and $R_4$ are each independently selected from the group consisting of hydrogen, alkyl, alkoxy, aryl, aryloxy, alkaryl, alkaryloxy, halogen, trihalomethyl, S(O)R, $SO_2$ NRR', $SO_3$ R, SR, $NO_2$, NRR', OH, CN, C(O)R, OC(O)R, NHC(O)R, $(CH_2)_n$ $CO_2$ R, and CONRR';

(c) $R_5$ is selected from the group consisting of hydrogen, alkyl, alkoxy, aryl, aryloxy, alkaryl, alkaryloxy, halogen, trihalomethyl, S(O)R, $SO_2$ NRR', $SO_3$ R, SR, $NO_2$, NRR', OH, CN, C(O)R, OC(O)R, NHC(O)R, $(CH_2)_n$ $CO_2$ R, CONRR', a six-membered heteroaryl ring system containing 1 or 2 N, O, or S atoms; and a six-membered aryl ring system; and (c) $R_6$, and $R_7$ are each independently selected from the group consisting of hydrogen, alkyl, alkoxy, aryl, aryloxy, alkaryl, alkaryloxy, halogen, trihalomethyl, S(O)R, $SO_2$ NRR', $SO_3$ R, SR, $NO_2$, NRR', OH, CN, C(O)R, OC(O)R, NHC(O)R, $(CH_2)_n$ $CO_2$ R, and CONRR', where R can be a wide variety of substituent groups.

More preferably, the compounds used in the invention have a structure set forth in Formula II,

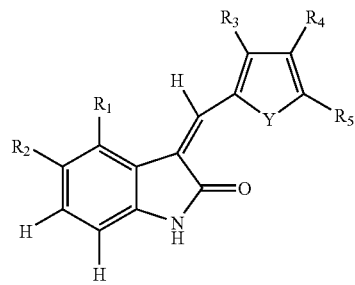

(II)

wherein (a) Y is selected from the group consisting of sulfur and nitrogen substituted with a hydrogen;

(b) $R_1$ is selected from the group consisting of hydrogen and methyl;

(c) $R_2$ is selected from the group consisting of
(i) hydrogen;
(ii) chlorine;
(iii) bromine;
(iv) a ketone of the formula —CH—$CH_3$,
(v) a sulfonamide of the formula —$SO_2NH_2$, or —$SO_2NCH_3CH_3$ (d) $R_3$, $R_4$, and $R_5$ are each independently selected from the group consisting of
(i) hydrogen;
(ii) methyl;
(iii) a carboxylic acid of formula —$(CH_2)_2$—COOH; and
(iv) $R_8$ and $R_9$ taken together form a six-membered saturated carbon ring.

Most preferably, the compound is one of the following:

Compound One, below:

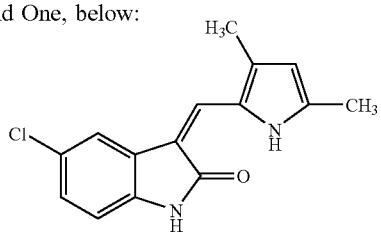

Compound Two, below:

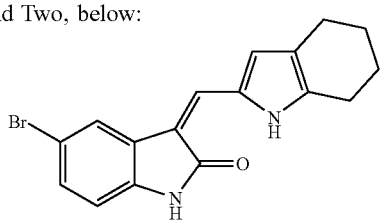

Compound Three, below:

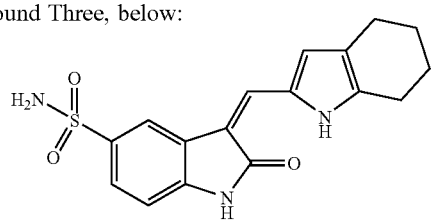

Compound Four, below:
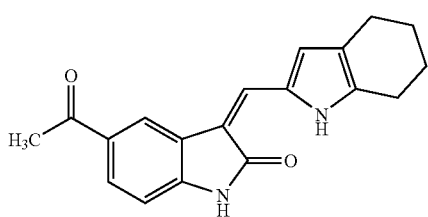
Compound Five, below:
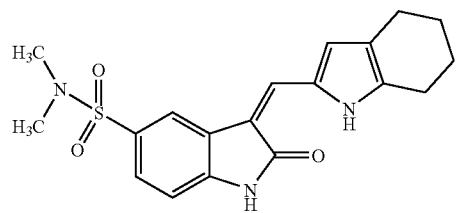
Compound Six, below:
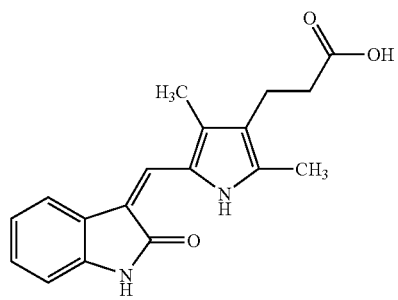
Compound Seven, below:
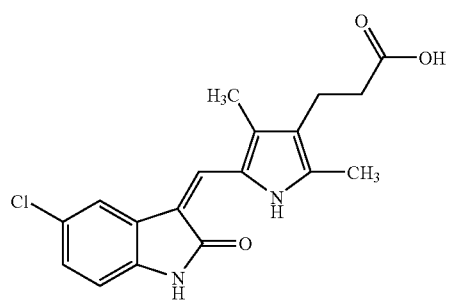
Compound Eight, below:
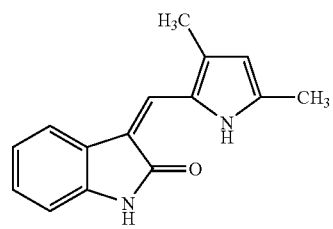
Compound Nine, below:
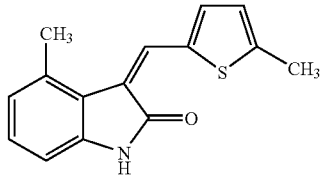
Compound Ten, below
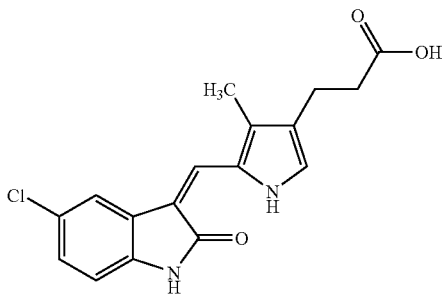
Compound Eleven, below:
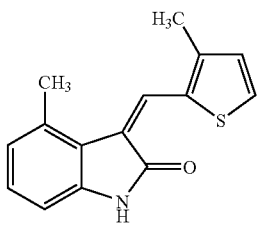
Compound Twelve, below:
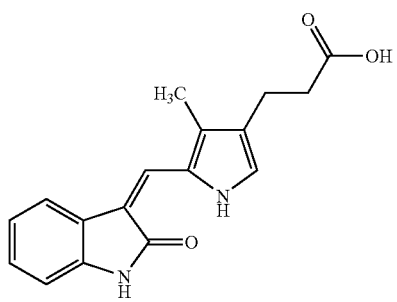
Compound Thirteen, below:
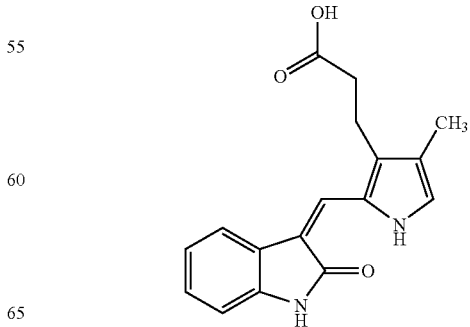

Compound Fourteen, below:

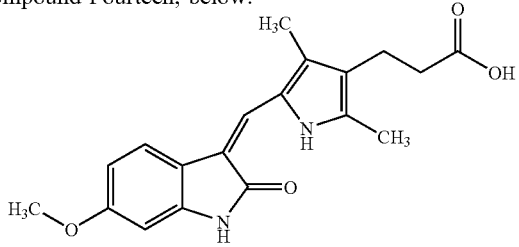

Compound Fifteen, below:

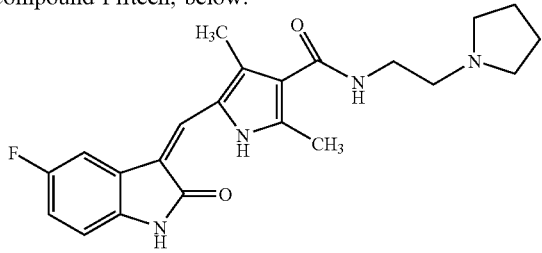

Compound Sixteen, below:

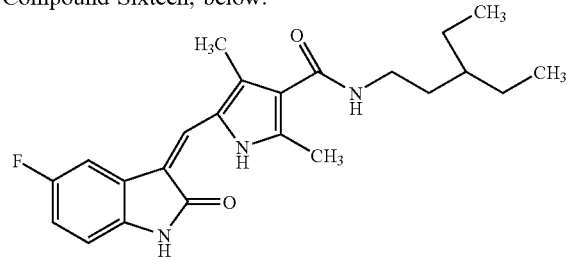

The term "oxindole" refers to an oxindole compound substituted with chemical substituents. Oxindole compounds are of the general structure shown in Formula III:

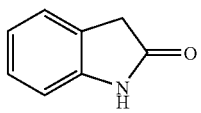

(III)

The term "substituted", in reference to the invention, refers to an oxindole compound that is derivatized with any number of chemical substituents.

The indolinone compounds of the invention preferably modulate the activity of the protein tyrosine kinase in vitro. These compounds preferably show positive results in one or more in vitro assays for an activity corresponding to treatment of the disease or disorder in question (such as the assays described in the Examples below). The protein tyrosine kinase which is modulated by the indolinone compounds of the invention is preferably the c-kit kinase. Examples of the procedures for and the results of such modulation are described in the Examples below.

The term "compound" means any identifiable molecule or a pharmaceutically acceptable salt, ester, amide, prodrug, isomer, or metabolite, thereof A "prodrug" refers to an agent which is converted into the parent drug in vivo. Prodrugs are often useful because, in some situations, they may be easier to administer than the parent drug. They may, for instance, be bioavailable by oral administration whereas the parent drug is not. The prodrug may also have improved solubility in pharmaceutical compositions over the parent drug. An example, without limitation, of a prodrug would be a compound of the present invention which is administered as an ester (the "prodrug") to facilitate transmittal across a cell membrane where water solubility is detrimental to mobility but then is metabolically hydrolyzed to the carboxylic acid, the active entity, once inside the cell where water solubility is beneficial.

A further example of a prodrug might be a short polypeptide, for example, without limitation, a 2–10 amino acid polypeptide, bonded through a terminal amino group to a carboxy group of a compound of this invention wherein the polypeptide is hydrolyzed or metabolized in vivo to release the active molecule.

The term "modulates" refers to altering the function of a protein kinase by increasing or decreasing the probability that a complex forms between a protein kinase and a natural binding partner. A modulator preferably increases the probability that such a complex forms between the protein kinase and the natural binding partner, more preferably increases or decreases the probability that a complex forms between the protein kinase and the natural binding partner depending on the concentration of the compound exposed to the protein kinase, and most preferably decreases the probability that a complex forms between the protein kinase and the natural binding partner. A modulator preferably activates the catalytic activity of a protein kinase, more preferably activates or inhibits the catalytic activity of a protein kinase depending on the concentration of the compound exposed to the protein kinase, or most preferably inhibits the catalytic activity of a protein kinase.

The term "complex" refers to an assembly of at least two molecules bound to one another. Signal transduction complexes often contain at least two protein molecules bound to one another.

The term "activates" refers to increasing the function of a protein kinase. The protein kinase function is preferably the interaction with a natural binding partner and most preferably catalytic activity.

The term "inhibit" refers to decreasing the function of a protein kinase. The protein kinase function is preferably the interaction with a natural binding partner and most preferably catalytic activity.

A protein kinase's natural binding partner can bind to a protein kinase's extracellular or intracellular region with high affinity. High affinity represents an equilibrium binding constant on the order of $10^{-6}$ M or less. In addition, a natural binding partner can also transiently interact with a protein kinase's extracellular or intracellular region and chemically modify it. Protein kinase natural binding partners are chosen from a group that includes, but is not limited to, SRC homology 2 (SH2) or 3 (SH3) domains, other phosphoryl tyrosine binding (PTB) domains, guanine nucleotide exchange factors, protein phosphatases, other protein kinases, and compounds such as ATP. Methods of determining changes in interactions between protein kinases and their natural binding partners are readily available in the art.

The term "related to" refers to a disease which has been shown to be accompanied by inappropriate c-kit kinase expression when compared to the same undiseased tissue isolated from an organism. The inappropriate expression can be an elevation of normal activities, a depression of normal activities, or the presence of c-kit kinase activity where none is normally found.

The term "in vitro" refers to when the c-kit kinase enzyme is tested outside of a living organism with a compound useful for this invention whereby such compounds are screened for efficaciousness. The term "in vitro" includes the use of tissue culture cells.

The term "promotes or disrupts the abnormal interaction" refers to a method that can be accomplished by administering a compound of the invention to cells or tissues in an organism. A compound can promote an interaction between a protein kinase and natural binding partners by forming favorable interactions with multiple atoms at the complex interface. Alternatively, a compound can inhibit an interaction between a protein kinase and natural binding partners by compromising favorable interactions formed between atoms at the complex interface. In preferred embodiments, the promotion or disruption of an abnormal interaction refers to the compound of the invention promoting a conformational change in one of the proteins.

In another aspect, the invention relates to synthesis of indolinone compounds described herein, in particular indolinones of Formula I, above, and especially Compounds One through Thirteen. The general scheme for the synthesis of representative indolinone compounds are set forth in the PCT publication U.S. Ser. No. 99/06468, filed Mar. 26, 1999 by Fong et al. and entitled METHODS OF MODULATING TYROSINE PROTEIN KINASE and the U.S. Pat. No. 5,792,783, issued Aug. 11, 1998 by Tang et al., entitled 3-HETEROARYL-2-INDOLINONE COMPOUNDS FOR THE TREATMENT OF DISEASE which are hereby incorporated by reference in their entirety including any drawings. Those skilled in the art know by reviewing the above reference which oxindoles and which aldehydes are to be reacted under which suitable conditions to form the compounds of the present invention.

The invention also features a method of identifying indolinone compounds, or compounds such as a pharmaceutically acceptable salt, ester, amide, prodrug, isomer, or metabolite thereof, that modulate the function of c-kit kinase, comprising the following steps: (a) contacting cells expressing the c-kit kinase with the compound; and (b) monitoring an effect upon the cells. The effect upon the cells is preferably a change or an absence of a change in cell phenotype, more preferably it is a change or an absence of a change in cell proliferation, even more preferably it is a change or absence of a change in the catalytic activity of the c-kit kinase, and most preferably it is a change or absence of a change in the interaction between the c-kit kinase with a natural binding partner, as described herein.

The term "monitoring" refers to observing the effect of adding the compound to the cells of the method. The "monitoring" can be effected by comparing test cells with control cells.

The term "effect" describes a change or an absence of a change in cell phenotype or cell proliferation. "Effect" can also describe a change or an absence of a change in the catalytic activity of the pro c-kit kinase. "Effect" can also describe a change or an absence of a change in an interaction between the c-kit kinase and a natural binding partner.

The term "cell phenotype" refers to the outward appearance of a cell or tissue or the function of the cell or tissue. Examples of cell phenotype are cell size (reduction or enlargement), cell proliferation (increased or decreased numbers of cells), cell differentiation (a change or absence of a change in cell shape, cell function, or differences in protein expression), cell survival, apoptosis (cell death), or the utilization of a metabolic nutrient (e.g., glucose uptake). Changes or the absence of changes in cell phenotype are readily measured by techniques known in the art.

In a preferred embodiment, the invention features a method for identifying the indolinones of the invention, comprising the following steps: (a) lysing the cells to render a lysate comprising c-kit kinase; (b) adsorbing the c-kit kinase to an antibody; (c) incubating the adsorbed c-kit kinase with a substrate or substrates; and (d) adsorbing a detecting antibody to the c-kit kinase. The effect upon the kinases is then monitored and the step of monitoring the effect on the kinases comprises measuring the phosphate concentration incorporated into c-kit kinase.

The term "antibody" refers to an antibody (e.g., a monoclonal or polyclonal antibody), or antibody fragment, having specific binding affinity to c-kit kinase or its fragment or to phosphotyrosine.

By "specific binding affinity" is meant that the antibody binds to target (c-kit kinase) polypeptides with greater affinity than it binds to other polypeptides under specified conditions. Antibodies having specific binding affinity to a c-kit kinase may be used in methods for detecting the presence and/or amount of a c-kit kinase in a sample by contacting the sample with the antibody under conditions such that an immunocomplex forms and detecting the presence and/or amount of the antibody conjugated to the c-kit kinase. Diagnostic kits for performing such methods may be constructed to include a first container containing the antibody and a second container having a conjugate of a binding partner of the antibody and a label, such as, for example, a radioisotope. The diagnostic kit may also include notification of an FDA approved use and instructions therefor.

The term "polyclonal" refers-to antibodies that are heterogenous populations of antibody molecules derived from the sera of animals immunized with an antigen or an antigenic functional derivative thereof For the production of polyclonal antibodies, various host animals may be immunized by injection with the antigen. Various adjuvants may be used to increase the immunological response, depending on the host species.

"Monoclonal antibodies" are substantially homogenous populations of antibodies to a particular antigen. They may be obtained by any technique which provides for the production of antibody molecules by continuous cell lines in culture. Monoclonal antibodies may be obtained by methods known to those skilled in the art. See, for example, Kohler, et al., *Nature* 256:495–497 (1975), and U.S. Pat. No. 4,376,110.

The term "antibody fragment" refers to a portion of an antibody, often the hypervariable region and portions of the surrounding heavy and light chains, that displays specific binding affinity for a particular molecule. A hypervariable region is a portion of an antibody that physically binds to the polypeptide target.

The summary of the invention described above is non-limiting and other features and advantages of the invention will be apparent from the following description of the preferred embodiments, and from the claims.

BRIEF DESCRIPTION OF THE FIGURES

FIG. 2 shows the effects of indolinone derivatives on the activity of c-kit kinase as measured by ELISA as described in Example I in the experimental section.

DETAILED DESCRIPTION OF THE INVENTION

Figure 1:
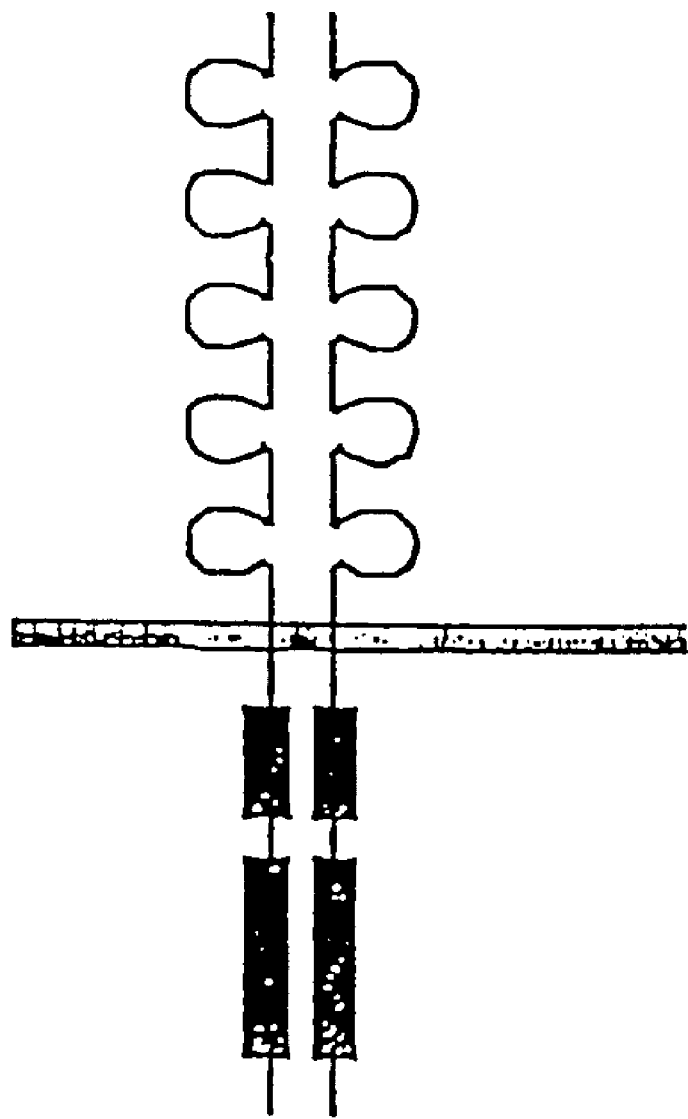
FIG. 1 is a schematic diagram showing the 5 immunoglobulin-like motifs in the extracellular domain and a cytoplasmic "split" kinase domain of c-kit kinase. The half-loops represent the immunoglobulin-like motifs, and the shaded boxes represent the conserved kinase region of the receptors.

The present invention relates to methods, compounds and compositions capable of regulating and/or modulating cellular signal transduction and, in preferred embodiments, c-kit kinase signal transduction.

Receptor kinase-mediated signal transduction is initiated by extracellular interaction with a specific growth factor (ligand), followed by receptor dimerization, transient stimulation of the intrinsic protein kinase activity, and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects to the extracellular microenvironment). See, Schlessinger and Ullrich, 1992, *Neuron* 9:303–391.

Kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis).

This invention is therefore directed to methods, compounds, and compositions which regulate, modulate and/or inhibit kinase signal transduction by affecting the enzymatic activity of receptor kinases and interfering with the signal transduced by such proteins. More particularly, the present invention is directed to methods, compounds and compositions which regulate, modulate and/or inhibit the c-kit receptor tyrosine kinase and/or other kinase mediated signal transduction pathways as a therapeutic approach to cure many kinds of solid tumors and leukemias, including but not limited to carcinoma, sarcoma, erythroblastoma, glioblastoma, meningioma, astrocytoma, melanoma and myoblastoma. Indications may include, but are not limited to lung cancers, including both small cell lung cancers and non-small cell lung cancers, brain cancers, bladder cancers, ovarian cancers, gastric cancers, pancreas cancers, colon cancers, blood cancers, and bone cancers. The present invention is also directed to the treatment and/or prevention of those conditions characterized by the overexpression of mast cells, or the inappropriate up-regulation of mast cells, including, but not limited to, mastocytosis, and allergy-associated chronic rhinitis, inflammation and asthma. These conditions are described in greater detail below.

1. Target Diseases to be Treated by the Compounds of the Invention.

The compounds described herein are useful for treating disorders related to unregulated kinase signal transduction, including cell proliferative disorders, fibrotic disorders and metabolic disorders. Cell proliferative disorders which can be treated or further studied by the present invention include cancers, and mast cell proliferative disorders.

PTKs have been associated with such cell proliferative disorders. For example, some members of the receptor tyrosine kinase (RTK) family have been associated with the development of cancer. Some of these receptors, like the EGFR (Tuzi, et al., 1991, *Br. J. Cancer* 63:227–233; Torp, et al., 1992, *APMIS* 100:713–719) HER2/neu (Slamon, et al., 1989, *Science* 244:707–712) and the PDGF—R (Kumabe, et al., 1992, *Oncogene* 7:627–633) are overexpressed in many tumors and/or persistently activated by autocrine loops. In fact, in the most common and severe cancers these receptor overexpressions (Akbasak and Suner-Akbasak, et al., 1992, *J. Neurol. Sci.* 111:119–133; Dickson, et al., 1992, *Cancer Treatment Res.* 61:249–273; Korc, et al., 1992, *J. Clin. Invest.* 90:1352–1360) and autocrine loops (Lee and Donoghue, 1992, *J. Cell. Biol.* 118:1057–1070; Korc, et al., supra; Akbasak and Suner-Akbasak, et al., supra) have been demonstrated. For example, the EGFR receptor has been associated with squamous cell carcinoma, astrocytoma, glioblastoma, head and neck cancer, lung cancer and bladder cancer. HER2 has been associated with breast, ovarian, gastric, lung, pancreas and bladder cancer. The PDGF—R has been associated with glioblastoma, lung, ovarian, melanoma and prostate cancer.

The c-kit receptor kinase has been associated with such cell proliferative disorders. For example, the c-kit kinase receptor has been found to be aberrantly expressed in over half the SCLC cells studied along with its ligand SCF (Hibi, et al., 1991, *Oncogene* 6:2291–2296). Potentially, inhibition of the c-kit kinase will improve the long term survival of patients with SCLC.

The presence of c-kit RTK and/or SCF has also been associated with other types of cancers, as described below. The association between abnormalities in RTKs and disease are not restricted to cancer, however. For example, the c-kit Receptor Kinase has been associated with immune diseases such as mastocytosis, asthmas and chronic rhinitis. Excessive activation of c-kit might be associated with diseases resulting from an over-abundance of mast cells. Mastocytosis is the term used to describe a heterogeneous series of disorders characterized by excessive mast cell proliferation (Metcalfe, 1991, *J. Invest. Derm* 93:2S-4S; Valent, 1996, *Wein/Klin Wochenschr* 108:385–397; and Golkar, et al., 1997, *Lancet* 349:1379–1385). Elevated c-kit expression was reported on mast cells from patients with aggressive mastocytosis, but not on mast cells from patients with indolent mastocytosis (Nagata, et al., 1998, *Leukemia* 12:175–181).

Additionally, mast cells and eosinophils represent key cells involved in allergy, inflammation and asthma (Thomas, et al., 1996, *Gen. Pharmacol* 27:593–597; Metcalfe, et al., 1997, *Physiol Rev* 77:1033–1079; Holgate, 1997, *CIBA Found. Symp.*; Naclerio, et al., 1997, *JAMA* 278:1842–1848 and Costa, et al., 1997, *JAMA* 278:1815–1822). SCF, and hence c-kit, directly and indirectly regulates activation of both mast cells and eosinophils, thereby influencing the primary cells involved in allergy and asthma through multiple mechanisms. Because of this mutual regulation of mast cell and eosinophil function, and the role that SCF can play in this regulation, inhibition of c-kit Kinase may provide a means to treat allergy-associated chronic rhinitis, inflammation and asthma.

II. c-kit Kinase

The c-kit kinase plays a critical role in the development of melanocytes, mast, germ and hematopoietic cells. The protein encoded by the Sl locus has been called kit ligand (KL), stem cell factor (SCF) or mast cell growth factor (MGF), based on its biological properties used to identify it (reviewed in Tsujimura, 1996, *Pathol Int* 46:933–938; Loveland, et al., 1997, *J. Endocrinol* 153:337–344; Vliagoftis, et al., 1997, *Clin Immunol* 100:435–440; Broudy, 1997, *Blood* 90:1345–1364; Pignon, 1997, *Hermatol Cell Ther* 39:1 14–116; and Lyman, et al., 1998, *Blood* 91:1101–1134.). For simplicity, we will use SCF to designate the ligand for the c-kit RTK. SCF is synthesized as a transmembrane protein with a molecular weight of 220 or 248 Dalton, depending on alternative splicing of the mRNA to encode exon 6. The larger protein can be proteolytically cleaved to form a soluble, glycosylated protein which noncovalently dimerizes. Both the soluble and membrane-bound forms of SCF can bind to and activate c-kit. For example, in the skin, SCF is predominantly expressed by fibroblasts, keratinocytes, and endothelial cells, which modulate the activity of melanocytes and mast cells expressing c-kit. In bone, marrow stromal cells express SCF and regulate hematopoiesis of c-kit expressing stem cells. In the gastrointestinal tract, intestinal epithelial cells express SCF and affect the interstitial cells of Cajal and intraepithelial lymphocytes. In the testis, sertoli cells and granulosa cells express SCF which regulates spermatogenesis by interaction with c-kit on germ cells.

a. Target Malignancies of the Present Invention Involving c-kit Kinase and/or SCF Aberrant expression and/or activation of c-kit has been implicated in a variety of tumors. Evidence for a contribution of c-kit to neoplastic pathology includes its association with leukemias and mast cell tumors, small cell lung cancer, testicular cancer, and some cancers of the gastrointestinal tract and central nervous system (see below). In addition, c-kit has been implicated in playing a role in carcinogenesis of the female genital tract (Inoue, et al., 1994, *Cancer Res.* 54(11):3049–3053), sarcomas of neuroectodermal origin (Ricotti, et al., 1998, *Blood* 91:2397–2405), and Schwann cell neoplasia associated with neurofibromatosis (Ryan, et al., 1994, *J. Neuro. Res.* 37:415–432).

Leukemias: SCF binding to the c-kit RTK protects hematopoietic stem and progenitor cells from apoptosis (Lee, et al., 1997, *J. Immunol.* 159:3211–3219), thereby contributing to colony formation and hematopoiesis. Expression of c-kit is frequently observed in acute myelocytic leukemia (AML), but is less common in acute lymphocytic leukemia (ALL) (for reviews, see Sperling, et al., 1997, *Haemat* 82:617–621; Escribano, et al., 1998, *Leuk. Lymph.* 30:459–466). Although c-kit is expressed in the majority of AML cells, its expression does not appear to be prognostic of disease progression (Sperling, et al., 1997, *Haemat* 82:617–621). However, SCF protected AML cells from apoptosis induced by chemotherapeutic agents (Hassan, et al., 1996, *Acta. Hem.* 95:257–262). Inhibition of c-kit by the present invention will enhance the efficacy of these agents and may induce apoptosis of AML cells.

The clonal growth of cells from patients with myelodysplastic syndrome (Sawada, et al., 1996, *Blood* 88:319–327) or chronic myelogenous leukemia (CML) (Sawai, et al., 1996, *Exp. Hem.* 2:116–122) was found to be significantly enhanced by SCF in combination with other cytokines. CML is characterized by expansion of Philadelphia chromosome positive cells of the marrow (Verfaillie, et al., 1998, *Leuk.* 12:136–138), which appears to primarily result from inhibition of apoptotic death (Jones, 1997, *Curr. Opin. Onc.* 9:3–7). The product of the Philadelphia chromosome, $p210^{BCR-ABL}$, has been reported to mediate inhibition of apoptosis (Bedi, et al., 1995, *Blood* 86:1148–1158). Since $p210^{BCR-ABL}$ and the c-kit RTK both inhibit apoptosis and $p62^{dok}$ has been suggested as a substrate (Carpino, et al., 1997, *Cell* 88:197–204), it is possible that clonal expansion mediated by these kinases occurs through a common signaling pathway. However, c-kit has also been reported to interact directly with $p210^{BCR-ABL}$ (Hallek, et al., 1996, *Brit. J. Haem.* 94:5–16), which suggests that c-kit may have a more causative role in CML pathology. Therefore, inhibition of c-kit kinase will prove useful in the treatment of the above disorders.

Gastrointestinal cancers: Normal colorectal mucosa does not express c-kit (Bellone, et al., 1997, *J. Cell Physiol.* 172:1–11). However, c-kit is frequently expressed in colorectal carcinoma (Bellone, et al., 1997, *J. Cell Physiol.* 172:1–11), and autocrine loops of SCF and c-kit have been observed in several colon carcinoma cell lines (Toyota, et al, 1993, *Turn Biol* 14:295–302; Lahm, et al., 1995, *Cell Growth & Differ* 6:1111–1118; Bellone, et al., 1997, *J. Cell Physiol.* 172:1–11). Furthermore, disruption of the autocrine loop by the use of neutralizing antibodies (Lahm, et al, 1995, *Cell Growth & Differ.* 6:1111–1118) and downregulation of c-kit and/or SCF significantly inhibits cell proliferation (Lahm, et al., 1995, *Cell Growth & Differ* 6:1111–1118; Bellone, et al., 1997, *J. Cell Physiol.* 172:1–11).

SCF/c-kit autocrine loops have been observed in gastric carcinoma cell lines (Turner, et al., 1992, *Blood* 80:374–381; Hassan, eta{, 1998, *Digest. Dis. Science* 43:8–14), and constitutive c-kit activation also appears to be important for gastrointestinal stromal tumors (GISTs). GISTs are the most common mesenchymal tumor of the digestive system. More than 90% of GISTs express c-kit, which is consistent with the putative origin of these tumor cells from interstitial cells of Cajal (ICCs) (Hirota, et al., 1998, *Science* 279:577–580). ICCs are thought to regulate contraction of the gastrointestinal tract, and patients lacking c-kit in their ICCs exhibited a myopathic form of chronic idiopathic intestinal pseudo-obstruction (Isozaki, et al, 1997, *Amer. J. of Gast.* 9 332–334). The c-kit expressed in GISTs from several different patients was observed to have mutations in the intracellular juxtamembrane domain leading to constitutive activation of this RTK (Hirota, et al., 1998, *Science* 279: 577–580). Hence, inhibition of c-kit kinase will be an efficacious means for the treatment of these cancers.

Testicular cancers: Male germ cell tumors have been histologically categorized into seminomas, which retain germ cell characteristics, and nonseminomas which can display characteristics of embryonal differentiation. Both seminomas and nonseminomas are thought to initiate from a preinvasive stage designated carcinoma in situ (CIS) (Murty, et al., 1998, *Sem. Oncol.* 25:133–144). Both c-kit and SCF have been reported to be essential for normal gonadal development during embryogenesis (Loveland, et al, 1997, *J. Endocrinol* 153:337–344). Loss of either the receptor or the ligand resulted in animals devoid of germ cells. In postnatal testes, c-kit has been found to be expressed in Leydig cells and spermatogonia, while SCF was expressed in Sertoli cells (Loveland, et al., 1997, *J. Endocrinol* 153:337–344). Testicular tumors develop from Leydig cells with high frequency in transgenic mice expressing human papilloma virus 16 (HPV16) E6 and E7 oncogenes (Kondoh, et al., 1991, *J. Virol.* 65:3335–3339; Kondoh, et al., 1994, *J. Urol.* 152:2151–2154). These tumors express both c-kit and SCF, and an autocrine loop may contribute to the tumorigenesis (Kondoh, et al., 1995, *Oncogene* 10:341–347) associated with cellular loss of functional p53 and the retinoblastoma gene product by association with E6 and E7 (Dyson, et al., 1989, *Science* 243:934–937; Wemess, et al., 1990, *Science* 248:76–79; Scheffner, et al., 1990, *Cell* 63:1129–1136). Defective signaling mutants of SCF (Kondoh, et al., 1995, *Oncogene* 10:341–347) or c-kit (Li, et al., 1996, *Canc. Res.* 56:4343–4346) inhibited formation of testicular tumors in mice expressing HPV16 E6 and E7. The c-kit kinase activation is pivotal to tumorigenesis in these animals and thus modulation of the c-kit kinase pathway by the present invention will prevent or treat such disorders.

Expression of c-kit on germ cell tumors shows that the receptor is expressed by the majority of carcinomas in situ and seminomas, but c-kit is expressed in only a minority of nonseminomas (Strohmeyer, et al., 1991, *Canc. Res.* 51:1811–1816; Rajpert-de Meyts, et al., 1994, *Int. J. Androl.* 17:85–92; Izquierdo, et al., 1995, *J. Pathol.* 177:253–258; Strohmeyer, et al., 1995, *J. Urol.* 153:511–515; Bokenmeyer, et al., 1996, *J. Cance. Res. Clin. Oncol.* 122:301–306; Sandlow, et al., 1996, *J. Androl.* 17:403–408). Therefore, inhibition of c-kit kinase will provide a valuable new means for treating these disorders.

CNS cancers: SCF and c-kit are expressed throughout the CNS of developing rodents, and the pattern of expression suggests a role in growth, migration and differentiation of neuroectodermal cells. Expression of both receptor and ligand have also been reported in the adult brain (Hamel, et al., 1997, *J. Neuro-Onc.* 35:327–333). Expression of c-kit has also been observed in normal human brain tissue (Tada, et al. 1994, *J. Neuro* 80:1063–1073). Glioblastomna and astrocytoma, which define the majority of intracranial tumors, arise from neoplastic transformation of astrocytes (Levin, et al., 1997, *Principles & Practice of Oncology:* 2022–2082). Expression of c-kit has been observed in glioblastoma cell lines and tissues (Berdel, et al., 1992, *Canc. Res.* 52:3498–3502; Tada, et al. 1994, *J. Neuro* 80:1063–1073; Stanulla, et al., 1995, *Act Neuropath* 89:158–165).

The association of c-kit with astrocytoma pathology is less clear. Reports of expression of c-kit in normal astrocytes have been made (Natali, et al., 1992, *Int. J. Canc.* 52:197–201), (Tada, et al. 1994, *J. Neuro* 80:1063–1073), while others report it is not expressed (Kristt, et al., 1993, *Neuro.* 33:106–115). In the latter case, high levels of c-kit expression in high grade tumors were observed (Kristt, et al, 1993, *Neuro.* 33:106–115), while the former groups were unable to detect any expression in astrocytomas. In addition, contradictory reports of c-kit and SCF expression in neuroblastomas also exist. One study found that neuroblastoma cell lines often express SCF, but rarely express c-kit. In primary tumors, c-kit was detected in about 8% of neuroblastomas, while SCF was found in 18% oftumors (Beck, etal., 1995, *Blood* 86:3132–3138). In contrast, other studies (Cohen, et al, 1994, *Blood* 84:3465–3472) have reported that all 14 neuroblastoma cell lines examined contained c-kit/SCF autocrine loops, and expression of both the receptor and ligand were observed in 45% of tumor samples examined. In two cell lines, anti-c-kit antibodies inhibited cell proliferation, suggesting that the SCF/c-kit autocrine loop contributed to growth (Cohen, et al, 1994, *Blood* 84:3465–3472). Hence, c-kit kinase inhibitors will prove therapeutically useful as a means to treat these cancers.

b. Target Mast Cell Diseases Involving c-kit Kinase and/or SCF to be Treated/Prevented by the Present Invention.

Mastocytosis: As mentioned above, SCF (also known as mast cell growth factor) stimulation of c-kit has been reported to be essential for the growth and development of mast cells (Hamel, et al., 1997, *J. Neuro-Onc.* 35:327–333; Kitamura, et al, 1995, *Int. Arch. Aller. Immunol.* 107:54–56). Mice with mutations of c-kit that attenuate its signaling activity have exhibited significantly fewer mast cells in their skin (Tsujimura, 1996, *Pathol Int* 46:933–938). Excessive activation of c-kit might be associated with diseases resulting from an over abundance of mast cells.

Mastocytosis is the term used to describe a heterogeneous series of disorders characterized by excessive mast cell proliferation (Metcalfe, 1991, *J. Invest. Derm* 93:2S-4S; Valent; 1996; Golkar, et al., 1997, *Lancet* 349:1379–1385). Mastocytosis is limited to the skin in the majority of patients, but can involve other organs in 15–20% of patients (Valent, 1996, *Wein/Klin Wochenschr* 108:385–397; Golkar, et al., 1997, *Lancet* 349:1379–1385). Even among patients with systemic mastocytosis, the disease can range from having a relatively benign prognosis to aggressive mastocytosis and mast cell leukemia. (Valent, 1996, *Wein/Klin Wochenschr* 108:385–397; Golkar, et al., 1997, *Lancet* 349: 1379–1385). c-kit has been observed on malignant mast cells from canine mast cell tumors (London, et al., 1996, *J. Compar. Pathol.* 115:399–414), as well as on mast cells from patients with aggressive systemic mastocytosis (Baghestanian, et al., 1996, *Leuk.:* 116–122; Castells, et al., 1996, *J. Aller. Clin. Immunol.* 98:831–840).

Elevated c-kit expression was reported on mast cells from patients with aggressive mastocytosis, but not on mast cells from patients with indolent mastocytosis (Nagata, et al., 1998, *Mastocytosis Leuk* 12:175–181). SCF has been shown to be expressed on stromal cells as a membrane-bound protein, and its expression can be induced by fibrogenic growth factors such as PDGF (Hiragun, et al. 1998). It has also been shown to be expressed on keratinocytes as a membrane-bound protein in normal skin. However, in the skin of patients with mastocytosis, an increased amount of soluble SCF has been observed (Longley, et al., 1993, *New Engl. J. Med.* 328:1302–1307).

Mast cell chymase has been reported to cleave membrane-associated SCF to a soluble and biologically active form. This mast cell-mediated process could serve to generate a feedback loop to enhance mast cell proliferation and function (Longley, et al., 1997, *Proc. Natl. Acad. Sci.* 94:9017–9021), and may be important for the etiology of mastocytosis. Transgenic mice overexpressing a form of SCF that could not be proteolytically released from keratinocytes did not develop mastocytosis, while similar animals expressing normal SCF in keratinocytes exhibited a phenotype resembling human cutaneous mastocytosis (Kunisada, et al., 1998, *J. Exp. Med.* 187:1565–1573). Formation of large amounts of soluble SCF can contribute to the pathology associated with mastocytosis in some patients and the present invention can treat or prevent such disorders by modulating the interaction between SCF and c-kit kinase. Several different mutations of the c-kit RTK that resulted in constitutive kinase activity have been found in human and rodent mast cell tumor cell lines (Furitsu, et al., 1993, *J. Clin. Invest.* 92:1736–1744; Tsujimura, et al., 1994, *Blood* 9:2619–2626; Tsujimura, et al., 1995, *Int. Arch. Aller. Immunol* 106:377–385; Tsujimura, 1996, *Pathol Int* 46:933–938). In addition, activating mutations of the c-kit gene have been observed in peripheral mononuclear cells isolated from patients with mastocytosis and associated hematologic disorders (Nagata, et al., 1998, *Mastocytosis Leuk* 12:175–181), and in mast cells from a patient with urticaria pigmentosa and aggressive mastocytosis (Longley, et al., 1996, *Nat. Gen.* 12:312–314). Inhibition of c-kit kinase will therefore prove to have an excellent therapeutic role in the treatment of these disorders.

In some patients, activating mutations of the c-kit RTK may be responsible for the pathogenesis of the disease and these patients can be treated, or their diseases prevented, by modulation of the SCF interaction with c-kit kinase. SCF activation of c-kit as been shown to prevent mast cell apoptosis which may be critical for maintaining cutaneous mast cell homeostasis (Iemura, et al., 1994, *Amer. J. Pathol* 144:321–328; Yee, et al., 1994, *J. Exp. Med.* 179:1777–1787; Mekori, et al., 1994, *J. Immunol* 153: 2194–2203; Mekori, et al., 1995, *Int. Arch. Allergy Immunol.* 107:137–138). Inhibition of mast cell apoptosis could lead to the mast cell accumulation associated with mastocytosis. Thus, observation of c-kit activation resulting from overexpression of the receptor, excessive formation of soluble SCF, or mutations of the c-kit gene that constitutively activate its kinase, provides a rationale that inhibition of the kinase activity of c-kit will decrease the number of mast cells and provide benefit for patients with mastocytosis.

Asthma & Allergy: Mast cells and eosinophils represent key cells in parasitic infection, allergy, inflammation, and asthma (Thomas, et al., 1996, *Gen. Pharmacol* 27:593–597; Metcalfe, et al., 1997, *Physiol Rev* 77:1033–1079; Holgate, 1997, *CIBA Found. Symp.*; Naclerio, et al., 1997, *JAMA* 278:1842–1848; Costa, et al, 1997, *JAMA* 278:1815–1822). SCF has been shown to be essential for mast cell development, survival and growth (Kitamura, et al., 1995, *Int. Arch. Aller. Immunol.* 107:54–56; Metcalfe, et al., 1997, *Physiol Rev* 77:1033–1079). In addition, SCF cooperates with the eosinophil-specific regulator, IL-5, to increase the development of eosinophil progenitors (Metcalf, et al., 1998, *Proc. Natl. Acad. Sci., USA* 95:6408–6412). SCF has also been reported to induce mast cells to secrete factors (Okayama, et al., 1997, *Int. Arch. Aller. Immunol.* 114:75–77; Okayama, et al., 1998, *Eur. J. Immunol.* 28:708–715) that promote the survival of eosinophils (Kay, et al., 1997, *Int. Arch. Aller. Immunol.* 113:196–199), which may contribute to chronic, eosinophil-mediated inflammation (Okayama, et al., 1997, *Int. Arch. Aller. Immunol.* 114:75–77; Okayama, et al., 1998, *Eur. J. Immunol.* 28:708–715). In this regard, SCF directly and indirectly regulates activation of both mast cells and eosinophils.

SCF induces mediator release from mast cells, as well as priming these cells for IgE-induced degranulation (Columbo, et al., 1992, *J. Immunol* 149:599–602) and sensitizing their responsiveness to eosinophil-derived granule major basic protein (Furuta, et al., 1998, *Blood* 92:1055–1061). Among the factors released by activated mast cells are IL-5, GM-CSF and TNF-α, which influence eosinophil protein secretion (Okayama, et al., 1997, *Int. Arch. Aller. Immunol.* 114:75–77; Okayama, et al., 1998, *Eur. J. Immunol.* 28:708–715). In addition to inducing histamine release from mast cells (Luckacs, et al., 1996, *J. Immunol.* 156:3945–3951; Hogaboam, et al., 1998, *J. Immunol.* 160:6166–6171), SCF promotes the mast cell production of the eosinophil chemotactic factor, eotaxin (Hogaboam, et al., 1998, *J. Immunol.* 160:6166–6171), and eosinophil infiltration (Luckacs, et al., 1996, *J. Immunol.* 156:3945–3951).

SCF also directly influences the adhesion of both mast cells (Dastych, et al., 1994, *J. Immunol.* 152:213–219; Kinashi, et al., 1994, *Blood* 83:1033–1038) and eosinophils (Yuan, et al., 1997, *J. Exp. Med.* 186:313–323), which in turn, regulates tissue infiltration. Thus, SCF can influence the primary cells involved in allergy and asthma through multiple mechanisms. Currently, corticosteroids are the most effective treatment for chronic rhinitis and inflammation associated with allergy (Naclerio, et al., 1997, *JAMA* 278:1842–1848; Meltzer, 1997, *Aller.* 52:33–40). These agents work through multiple mechanisms including reduction of circulating and infiltrating mast cells and eosinophils, and diminished survival of eosinophils associated with inhibition of cytokine production (Meltzer, 1997, *Aller.* 52:33–40). Steroids have also been reported to inhibit the expression of SCF by fibroblasts and resident connective tissue cells, which leads to diminished mast cell survival (Finotto, et al., 1997, *J. Clin. Invest.* 99 1721–1728). Because of the mutual regulation of mast cell and eosinophil function, and the role that SCF can play in this regulation, inhibition of c-kit kinase will provide a means to treat allergy-associated chronic rhinitis, inflammation and asthma.

c. Identification of Agonists and Antagonists to the c-kit Receptor

In view of the deduced importance of RTKs in the control, regulation and modulation of endothelial cell proliferation and potentially carcinogenesis, many attempts have been made to identify RTK "inhibitors" using a variety of approaches. These include the use of mutant ligands (U.S. Pat. No. 4,966,849); soluble receptors and antibodies (Application No. WO 94/10202; Kendall and Thomas, 1994, *Proc. Natl. Acad. Sci. USA* 90:10705–10709; Kim, et al., 1993, *Nature* 362:841–844); and RNA ligands (Jellinek, et al., 1994, *Biochemistry* 33:10450–10456).

Furthermore, kinase inhibitors (WO 94/03427; WO 92/21660; WO 91/15495; WO 94/14808; U.S. Pat. No. 5,330,992; Mariani, et al., 1994, *Proc. Am. Assoc. Cancer Res.* 35:2268), and inhibitors acting on receptor kinase signal transduction pathways, such as protein kinase C inhibitors have been identified (Schuchter, et al., 1991, *Cancer Res.* 51:682–687); Takano, et al., 1993, *Mol. Bio. Cell* 4:358A; Kinsella, et al., 1992, *Exp. Cell Res.* 199: 56–62; Wright, et al., 1992, *J. Cellular Phys.* 152:448–57).

More recently, attempts have been made to identify small molecules which act as kinase inhibitors for use in the treatment of cancer. Consequently, there is an unmet need for the identification and generation of effective small compounds which selectively inhibit the signal transduction of the c-kit RTK in order to effectively and specifically suppress this autocrine loop.

Some of the compounds of the present invention demonstrate excellent activity in biological assays and thus these compounds and related compounds are expected to be effective in treating c-kit RTK-related disorders such as those described above. Additionally, the assays and conditions described herein can be utilized to identify further modulators of c-kit kinase functions.

III. Biological Activity of the Compounds of the Invention

The indolinone compounds of the present invention were tested for their ability to inhibit most of protein kinase activity. The biological assays and results of these inhibition studies are reported herein. The methods used to measure indolinone compound modulation of protein kinase function are similar to those described in International Publication No. WO 98/07695, published Mar. 26, 1998, by Tang et al., and entitled "INDOLINONE COMBINATORIAL LIBRARIES AND RELATED PRODUCTS AND METHODS FOR THE TREATMENT OF DISEASE," and U.S. Pat. No. 5,792,783, issued Aug. 11, 1998 by Tang et al., entitled 3-HETEROARYL-2-INDOLINONE COMPOUNDS FOR THE TREATMENT OF DISEASE with respect to the high throughput aspect of the method. The WO 98/07695 publication is incorporated herein by reference in its entirety, including any drawings.

IV. Pharmaceutical Formulations and Routes of Administration

The compounds described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., latest edition.

a) Routes of Administration

Suitable routes of administration may, for example, include oral, rectal, transmucosal, or intestinal administration; parenteral delivery, including intramuscular, subcutaneous, intravenous, intramedullary injections, as well as intrathecal, direct intraventricular, intraperitoneal, intranasal, or intraocular injections.

Alternately, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

b) Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by mixing one or more solid excipients with one or more compounds of the invention, optionally grinding the resulting mixture, and processing the mixture of granules, after adding suitable auxiliaries, if desired, to obtain tablets or dragee cores. Suitable excipients are, in particular, fillers-such as sugars, including lactose, sucrose, mannitol, or sorbitol; cellulose preparations such as, for example, maize starch, wheat starch, nice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant Polysorbate 80, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of Polysorbate 80; the fraction size of polyethylene glycol may be varied; other biocompatible polymers may replace polyethylene glycol, e.g., polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

Many of the PTK modulating compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents than are the corresponding free base forms.

c) Effective Dosage.

Pharmaceutical compositions suitable for use in the present invention include compositions where the active ingredients are contained in an amount effective to achieve its intended purpose. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

For any compound used in the methods of the invention, the therapeutically effective dose can be estimated initially from cell culture assays. For example, a dose can be formulated in animal models to achieve a circulating concentration range that includes the $IC_{50}$ as determined in cell culture (i.e., the concentration of the test compound which achieves a half-maximal inhibition of the PTK activity). Such information can be used to more accurately determine useful doses in humans.

Toxicity and therapeutic efficacy of the compounds described herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds which exhibit high therapeutic indices are preferred. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p.1).

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g., the concentration necessary to achieve 50–90% inhibition of the kinase using the assays described herein. Dosages necessary to achieve the MEC will depend on individual characteristics and route of administration. However, HPLC assays or bioassays can be used to determine plasma concentrations.

Dosage intervals can also be determined using MEC value. Compounds should be administered using a regimen which maintains plasma levels above the MEC for 10–90% of the time, preferably between 30–90% and most preferably between 50–90%.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

d) Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the compound for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

Additional methods of preparing pharmaceutical formulations of the compounds, methods of determining the amounts of compounds to be administered to a patient, and modes of administering compounds to an organism are disclosed in International patent publication number WO 96/22976, by Buzzetti, et ai., and entitled "Hydrosoluble 3-Arylidene-2-Oxindole Derivatives as Tyrosine Kinase Inhibitors," published Aug. 1, 1996, which is incorporated herein by reference in its entirety, including any drawings.

Those skilled in the art will appreciate that such descriptions are applicable to the present invention and can be easily adapted to it.

EXAMPLES

The examples below are non-limiting and are merely representative of various aspects and features of the present invention. The examples describe methods for synthesizing compounds of the invention and methods for measuring an effect of a compound on the function of protein kinases.

The cells used in the methods are available commercially or from academic labs or were engineered from commercially available cells. The nucleic acid vectors harbored by the cells are also commercially available and the sequences of genes for the various protein kinases are readily accessible in sequence data banks. Thus, a person of ordinary skill in the art can readily recreate the cell lines in a timely manner by combining the commercially available cells, the commercially available nucleic acid vectors, and the protein kinase genes using techniques readily available to persons of ordinary skill in the art.

Assay Procedures

The following in vitro assays may be used to determine the level of activity and effect of the different compounds of the present invention on one or more of the PKs. Similar assays can be designed along the same lines for any PK using techniques well known in the art.

The cellular/catalytic assays described herein are performed in an ELISA format. The general procedure is a follows: a compound is introduced to cells expressing the test kinase, either naturally or recombinantly, for some period of time after which, if the test kinase is a receptor, a ligand known to activate the receptor is added. The cells are lysed and the lysate is transferred to the wells of an ELISA plate previously coated with a specific antibody recognizing the substrate of the enzymatic phosphorylation reaction. Non-substrate components of the cell lysate are washed away and the amount of phosphorylation on the substrate is detected with an antibody specifically recognizing phosphotyrosine compared with control cells that were not contacted with a test compound. The assay could also be adapted to detection by Western blotting.

The cellular/biologic assays described herein measure the amount of DNA made in response to activation of a test kinase, which is a general measure of a proliferative response. The general procedure for this assay is as follows: a compound is introduced to cells expressing the test kinase, either naturally or recombinantly, for some period of time after which, if the test kinase is a receptor, a ligand known to activate the receptor is added. After incubation at least overnight, a DNA labeling reagent such as bromodeoxyuridine (BrdU) or 3H-thymidine is added. The amount of labeled DNA is detected with either an anti-BrdU antibody or by measuring radioactivity and is compared to control cells not contacted with a test compound.

Cellular/Catalytic Assays

Enzyme linked immunosorbent assays (ELISA) may be used to detect and measure the presence of PK activity. The ELISA may be conducted according to known protocols which are described in, for example, Voller, et al., 1980, "Enzyme-Linked Immunosorbent Assay," In: *Manual of Clinical Immunology*, 2d ed., edited by Rose and Friedman, pp. 359–371 Am. Soc. Of Microbiology, Washington, D.C.

The disclosed protocol may be adapted for determining activity with respect to a specific PK, such as c-kit kinase. The preferred protocols for conducting the ELISA experiments for the specific PKs, c-kit kinase, is provided below. Adaptation of these protocols for determining a compound's activity for other members of the RTK family, as well as for CTKs and STKs, is well within the scope of knowledge of those skilled in the art.

Example 1

The Activity of the Compounds of the Invention

The biochemical activity of some of the compounds of the invention were tested using the assays described. The $IC_{50}$ values were measured for several of the compounds of the invention. The results are shown in FIG. 2.

A. Materials and Reagents

1) HNTG: 5× stock concentration: 100 mM HEPES pH 7.2, 750 mM NaCl, 50% glycerol, 2.5% Triton X-100.
2) PBS (Dulbecco's Phosphate-Buffered Saline): Gibco Catalog # 450–1300EB
3) 1× Blocking Buffer: 10 mM TRIS-pH 7.5, 1% BSA, 100 mM NaCl, 0.1% Triton X-100
4) 1× Kinase Buffer: 25 mM HEPES, 100 mM NaCl, 10 mM Mg $Cl_2$, 6 mM Mn $Cl_2$.
5) PMSF Stock Solution=100 mM (Sigma Catalog # P-7626)
6) 10 mM ATP (Bacterial source) Sigma A-7699, 5 g.
7) UB40 anti-phosphotyrosine mAb.
8) HRP conjugated sheep anti-Mouse IgG. (Amersham NA 931)
9) ABTS (5Prime-3Prime 7-579844)
10) TRIS HCL: Fisher BP 152-5
11) NaCl: Fisher S271-10
12) Triton X-100: Fisher BP151-100
13) $Na_3VO_4$: Fisher S454-50
14) $MgCl_2$: Fisher M33-500
15) $MnCl_2$: Fisher M87-500
16) HEPES: Fisher BP310-500
17) Albumin, Bovine (BSA): Sigma A-8551
18) TBST Buffer: 50 mM Tris pH 7.2, 150 mM NaCl, 0.1% Triton X-100.
19) Goat affinity purified antibody Rabbit IgG (whole molecule): Cappel 55641.
20) Anti Kit (C-20) rabbit polyclonal IgG antibody: Santa Cruz sc-168
21) Kit/CHO cells: CHO cells stably expressing GyrB/Kit, which are grown in standard CHO medium, supplemented with 1 mg/ml G418
22) Indolinone Compounds: The indolinone compounds were synthesized as set forth in the following application: PCT application No. U.S. Ser. No. 99/06468, filed Mar. 26, 1999 by Fong, et al. and entitled METHODS OF MODULATING TYROSINE PROTEIN KINASE which is hereby incorporated by reference in its entirety including any drawings.

B. Procedure

All of the following steps are conducted at room temperature unless it is specifically indicated. All ELISA plate washing is by rinsing 4× with TBST.

Kit Cell Lysis

This procedure is performed 1 hour prior to the start of receptor capture.

1) Wash a >95% confluent 15 cm dish with PBS and aspirate as much as possible.
2) Lyse the cells with 3 ml of 1× HNTG containing 1 mM PMSF/15 cm dish. Scrape the cells from the plate and transfer to a 50 ml centrifuge tube.

3) Pool supernatants, and allow to sit, on ice, for one hour with occasional vortexing. Failure to do so with result in an increased background.(approximately 3-fold higher).

4) Balance tubes and centrifuge at 10,000× g for 10 min at 4° C. Remove an aliquot for protein determination 5) Perform protein determination as per the SOP for protein determination using the bicinchoninic acid (BCA) method.

ELISA Procedure

1) Coat Corning 96-well ELISA plates with 2 µg per well Goat anti-rabbit antibody in PBS for a total well volume of 100 µl. Store overnight at 4° C.

2) Remove unbound Goat anti-rabbit antibody by inverting plate to remove liquid.

3) Add 100 µl of Blocking Buffer to each well. Shake at room temperature for 60 min.

4) Wash 4× with TBST. Pat plate on a paper towel to remove excess liquid and bubbles 5) Add 0.2 µg per well of Rabbit anti-Kit antibody diluted in TBST for a total well volume of 100 µl. Shake at room temperature for 60 min.

6) Dilute lysate in HNTG (180 µg lysate/100 µl)

7) Add 100 µl of diluted lysate to each well. Shake at room temperature for 60 min.

8) Wash 4× with TBST. Pat plate on a paper towel to remove excess liquid and bubbles 9) Dilute compounds/extracts (or as stated otherwise) in 1× kinase buffer, with 5 µM ATP in a polypropylene 96 well plate 10) Transfer 100 µl of diluted drug to ELISA plate wells. Incubate at room temperature with shaking for 60 min.

11) Stop reaction with the addition of 10 µl of 0.5 M EDTA. Plate is now stable for a reasonable period of time.

12) Wash 4× with TBST. Pat plate on a paper towel to remove excess liquid and bubbles 13) Add 100 µl per well of UB40 (1:2000 dilution in TBST). Incubate 60 min at room temperature, with shaking.

14) Wash 4× with TBST. Pat plate on a paper towel to remove excess liquid and bubbles 15) Add 100 µl per well of sheep anti-mouse IgG—HRP (1:5000 dilution in TBST). Incubate 60 min at room temperature, with shaking.

16) Wash 4× with TBST. Pat plate on a paper towel to remove excess liquid and bubbles 17) Add 100 µl per well of ABTS. Incubate with shaking for 15–30 min.

18) Read assay on Dynatech MR7000 ELISA reader

Test Filter=410 nm

Reference Filter=630 nm

Example 2

The Activity of the Compounds of the Invention

The biochemical activity of two of the compounds of the invention were tested using the assays described below.

Methods:

Cell Lines

MO7E cells, a human myeloid leukemia cell line, were maintained in RPMI-1640 medium supplemented with 10% fetal calf serum and 10 ng/ml each IL-3 and GM-CSF.

Detection of c-kit Tyrosine Phosphorylation

MO7E cells were serum starved overnight in 0.1% serum. Cells were pre-treated with Compound Eight for 2 hours, or with Compound Six for 22 hours (concurrent with serum starvation), prior to ligand stimulation. Cells were stimulated with 250 ng/ml rh-SCF for 15 minutes. Following stimulation, cells were lysed and immunoprecipitated with an anti-c-kit antibody. Phosphotyrosine and protein levels were determined by western blotting.

MTT Proliferation Assay

MO7E cells were serum starved and pre-treated with compound as described for the phosphorylation experiments. Cells were plated@ $4 \times 10^5$ cells/well in a 96 well dish, in 100 µl RPMI+10% serum. rh-SCF (100 ng/mL) was added and the plate was incubated for 48 hours. After 48 hours, 10 µl of 5 mg/ml MTT [3-(4,5-dimethythiazol-2-yl)-2,5-diphenyl tetrazolium bromide) was added and allowed to incubate for 4 hours. Acid isopropanol (100 µl of 0.04N HCl in isopropanol) was added and the optical density was measured at a wavelength of 550 nm.

Apoptosis Assays

MO7E cells were incubated +/− SCF and +/− compound (Compound Six or Compound Eight@ 5 and 25 µM) in 10% FBS with rh-GM-CSF(10 ng/mL) and rh-IL-3 (10 ng/mL). Samples were assayed at 24 and 48 hours. To measure activated caspase-3, samples were washed with PBS and permeabilized with ice-cold 70% ethanol. The cells were then stained with PE-conjugated polyclonal rabbit anti-active caspase-3 and analyzed by FACS. To measure cleaved PARP, samples were lysed and analyzed by western blotting with an anti-PARP antibody.

Inhibition of Biological Functions of c-kit by Compound Eight and Compound Six

Results:

Inhibition of Tyrosine Phosphorylation of c-kit

Compound Eight and Compound Six inhibit tyrosine phosphorylation of c-kit in MO7E cells, a human myeloid leukemia cell line, in response to ligand stimulation with stem cell factor (SCF). In Compound Eight treated cells, no inhibition of phosphorylation was observed at 0.01 µM, partial inhibition was observed at 0.1 µM, and complete inhibition was observed at 1 and 10 µM. In Compound Six treated cells, no inhibition of c-kit tyrosine phosphorylation was observed at 0.01 µM or 0.1 µM, partial inhibition was observed at 1 µM, and complete inhibition was observed at 10 µM.

Inhibition of c-kit Mediated Proliferation

Compound Eight and Compound Six also inhibit c-kit mediated signaling in MO7E cells in an MTT proliferation assay. The $IC_{50}$ value for Compound Eight inhibition of proliferation is approximately 0.5–1.0 µM, and the $IC_{50}$ value for Compound Six is approximately 5–7 µM.

Induction of Apoptosis

Compound Eight and Compound Six also induce apoptosis in MO7E cells, in a dose and time dependent fashion. Apoptosis was assessed with two assays: a FACS analysis with an antibody that recognizes activated caspase-3 in cells, which is induced during apoptosis, and a western blotting assay that detects a cleaved fragment of poly (ADP-ribose) polymerase, also induced during apoptosis.

Using the caspase-3 assay, an approximately 50% increase in the number of apoptotic cells was observed at 48 hours, upon SCF stimulation and 25 µM Compound Eight treatment, compared to untreated SCF stimulated cells. A slight effect was observed at 48 hours with 25 µM Compound Eight in the absence of SCF stimulation. Treatment for 24 hours with 25 μM Compound Eight (+/− SCF stimulation), resulted in a measurable but smaller number of apoptotic cells.

Treatment of cells with 5 μM Compound Eight for 24 or 48 hours (+/− SCF stimulation) also resulted in a measurable but smaller number of apoptotic cells.

Similar results were obtained for Compound Six, with the exception of no effect observed with 5 μM Compound Six at 24 hours, with or without SCF stimulation.

Using the PARP assay, treatment with 25 μM Compound Eight for 48 hours resulted in the greatest increase in the amount of cleaved PARP. The effect was augmented slightly with SCF stimulation. The 24 hour sample treated with 25μM Compound Eight was similar to the 48 hour sample.

Treatment with 5 μM Compound Eight, at both timepoints, resulted in a very minimal increase in cleaved PARP.

Similar results were obtained for Compound Six.

Conclusion

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine-and claims for X being bromine and chlorine are fully described.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims.

What is claimed is:

1. A method for treating an abnormal condition associated with an aberration in a signal transduction pathway mediated by a c-kit kinase in an organism, comprising administering to said organism a therapeutically effective amount of an indolinone compound of the following formula that inhibits, in vitro, the catalytic activity of c-kit kinase:

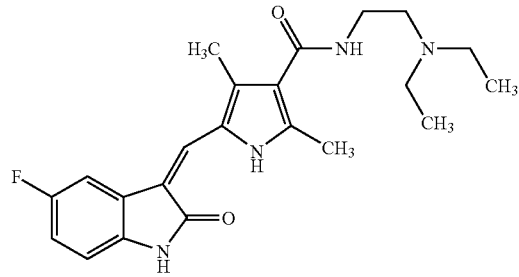

wherein the abnormal condition is one or more gastrointestinal stromal tumors.

2. A method for treating an abnormal condition associated with an aberration in a signal transduction pathway mediated by a c-kit kinase in an organism, comprising administering to said organism a therapeutically effective amount of an indolinone compound of the following formula that inhibits, in vitro, the catalytic activity of c-kit kinase:

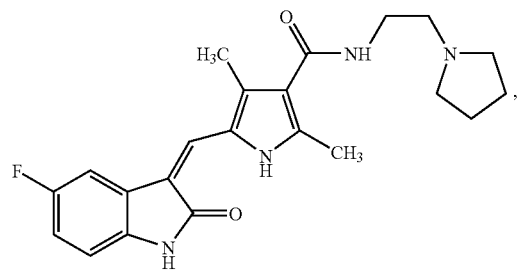

wherein the abnormal condition is mastocytosis.

3. A method for treating an abnormal condition associated with an aberration in a signal transduction pathway mediated by a c-kit kinase in an organism, comprising administering to said organism a therapeutically effective amount of an indolinone compound that inhibits, in vitro, the catalytic activity of c-kit kinase selected from the group consisting of:

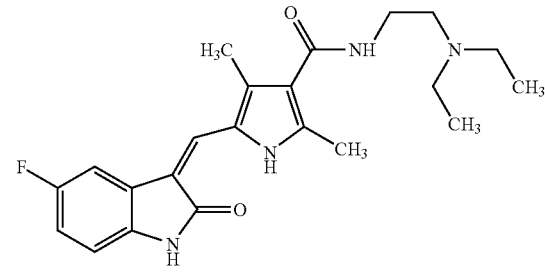

and

-continued

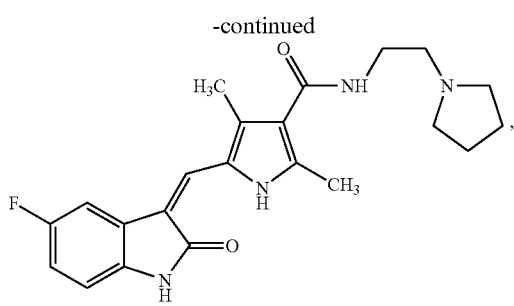

wherein the abnormal condition is allergy-associated chronic rhinitis, inflammation or asthma.

4. A method for treating an abnormal condition associated with an aberration in a signal transduction pathway mediated by a c-kit kinase in an organism, comprising administering to said organism a therapeutically effective amount of an indolinone compound of the following formula that inhibits, in vitro, the catalytic activity of c-kit kinase:

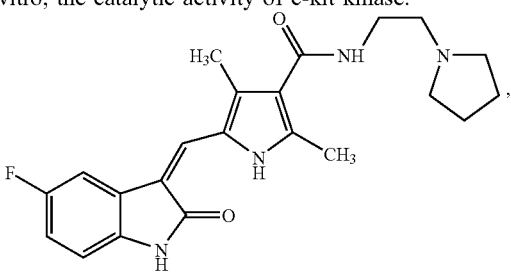

wherein the abnormal condition is one or more mast cell tumors.

* * * * *

UNITED STATES PATENT AND TRADEMARK OFFICE
CERTIFICATE OF CORRECTION

| | | |
|---|---|---|
| PATENT NO. | : 7,211,600 B2 | |
| APPLICATION NO. | : 11/205474 | |
| DATED | : May 1, 2007 | |
| INVENTOR(S) | : Ken Lipson et al. | |

Page 1 of 3

It is certified that error appears in the above-identified patent and that said Letters Patent is hereby corrected as shown below:

ON THE TITLE PAGE:

Item (60):

Please delete "Provisional application No. 60/171,963, filed Dec. 22, 1999." and insert -- Provisional application No. 60/171,693, filed Dec. 22, 1999. --

In the Specification, Column 7, Line 15:

Please delete "U599/06468" and insert -- US99/06468 --

In the Specification, Column 7, Line 16:

Please delete "26,1999" and insert -- 26, 1999 --

In the Specification, Column 7, Line 17:

Please delete "KJNASE" and insert -- KINASE --

In the Specification, Column 7, Line 19:

Please delete "Tang,è/ al." and insert -- Tang, et al. --

In the Specification, Column 7, Line 20:

Please insert -- (3) -- between the words ""INHIBITORS," and "U.S."

Signed and Sealed this
Tenth Day of April, 2012

David J. Kappos
*Director of the United States Patent and Trademark Office*

CERTIFICATE OF CORRECTION (continued)

In the Specification, Column 7, Line 25:

Please delete "MDOLI" and insert -- INDOLI --

In the Specification, Column 8, Line 25:

Please delete "-CH-CH$_3$" and insert -- -CO-CH$_3$ --

In the Specification, Column 11, Line 25:

Please delete " 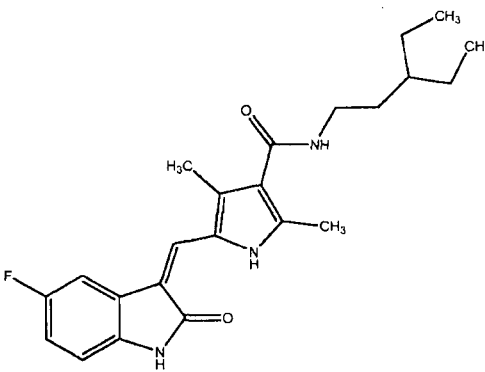 " and insert -- 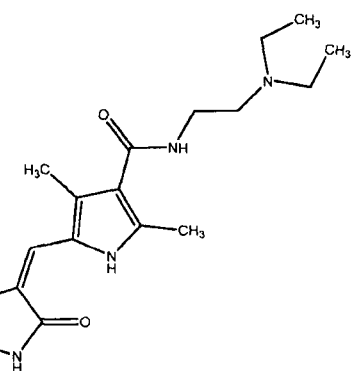 --

In the Specification, Column 11, Line 61:

Please delete "thereof" and insert -- thereof. --

In the Specification, Column 14, Line 33:

Please delete "thereof" and insert -- thereof. --

In the Specification, Column 15, Line 4:

Please delete "methods,.compounds" and insert -- methods, compounds --

In the Specification, Column 18, Line 21:

Please delete "eta{," and insert -- et al., --

CERTIFICATE OF CORRECTION (continued)
U.S. Pat. No. 7,211,600 B2

In the Specification, Column 18, Line 63:

Please delete "Wemess" and insert -- Werness --

In the Specification, Column 19, Line 44:

Please delete "oftumors" and insert -- of tumors --

In the Specification, Column 19, Line 45:

Please delete "etal." and insert -- et al. --

In the Specification, Column 28, Line 51:

Please delete "U.S. Ser. No. 99/06468" and insert -- US99/06468 --

In the Specification, Column 29, Line 4:

Please delete "10,000×" and insert -- 10,000 × --

In the Specification, Column 29, Line 5:

Please delete "4° C" and insert -- 4 °C --

In the Specification, Column 29, Line 10:

Please delete "Coming" and insert -- Corning --

In the Specification, Column 29, Line 12:

Please delete "4° C" and insert -- 4 °C --

In the Specification, Column 30, Line 10:

Please delete "plated@" and insert -- plated @ --

In the Specification, Column 30, Line 21:

Please delete "Eight@" and insert -- Eight @ --